(12) United States Patent
Lee et al.

(10) Patent No.: US 10,828,088 B2
(45) Date of Patent: *Nov. 10, 2020

(54) RADIO FREQUENCY ABLATION DEVICE FOR THE DESTRUCTION OF TISSUE MASSES

(71) Applicant: Acessa Health Inc., Austin, TX (US)

(72) Inventors: Bruce B. Lee, Austin, TX (US);
Gordon E. Epstein, Austin, TX (US);
Adam Hagmann, Austin, TX (US);
Jeffrey M. Cohen, Austin, TX (US)

(73) Assignee: ACESSA HEALTH INC., Austin, TX (US)

( * ) Notice: Subject to any disclaimer, the term of this patent is extended or adjusted under 35 U.S.C. 154(b) by 338 days.

This patent is subject to a terminal disclaimer.

(21) Appl. No.: 15/497,076

(22) Filed: Apr. 25, 2017

(65) Prior Publication Data

US 2017/0333116 A1     Nov. 23, 2017

Related U.S. Application Data

(63) Continuation of application No. 13/323,722, filed on Dec. 12, 2011, now Pat. No. 9,662,166, which is a
(Continued)

(51) Int. Cl.
*A61B 18/14*     (2006.01)

(52) U.S. Cl.
CPC .... *A61B 18/1477* (2013.01); *A61B 2018/143* (2013.01); *A61B 2018/1425* (2013.01);
(Continued)

(58) Field of Classification Search
CPC ........ A61B 18/1477; A61B 2018/1425; A61B 2018/143; A61B 2018/1432; A61B 2018/1475

See application file for complete search history.

(56) References Cited

U.S. PATENT DOCUMENTS

| 35,330 A | 5/1862 | Silvester |
|---|---|---|
| 3,991,770 A | 11/1976 | Leveen |

(Continued)

FOREIGN PATENT DOCUMENTS

| DE | 2124684 | 11/1972 |
|---|---|---|
| WO | WO 2003/090636 | 11/2003 |

(Continued)

OTHER PUBLICATIONS

Bergamini, MD. et al. "Laparoscopic radiofrequency thermal ablation: A new approach to symptomatic uterine myomas," American Journal of Obstetrics and Gynecology, 192:768-73 Varese, Italy, Mar. 1, 2005.

*Primary Examiner* — Michael F Peffley
(74) *Attorney, Agent, or Firm* — Vista IP Law Group, LLP

(57) ABSTRACT

The inventive ablation element comprises an elongated cannula having a proximal end and a distal end. The cannula defines an internal lumen within the cannula and a cannula axis. A plurality of conductors contained within the lumen, each of the conductors has a proximal end proximate the proximal end of the cannula, and a distal end proximate the distal end of the cannula. A plurality of ablation stylets each has a proximal end and a distal end, and each coupled at the respective proximal end of the stylet to the distal end of a respective conductor, the stylets comprise a deflectable material, the conductors together with their respective stylets being mounted for axial movement. A trocar point defined proximate the distal end of the cannula.

17 Claims, 29 Drawing Sheets

Related U.S. Application Data continuation of application No. 11/173,928, filed on Jul. 1, 2005, now Pat. No. 8,080,009.

(52) U.S. Cl.
CPC ............. A61B 2018/1432 (2013.01); A61B 2018/1475 (2013.01)

(56) References Cited

U.S. PATENT DOCUMENTS

| | | | |
|---|---|---|---|
| 4,016,886 A | 4/1977 | Doss et al. | |
| 4,074,718 A | 2/1978 | Morrison | |
| 4,080,959 A | 3/1978 | Leveen | |
| 4,095,602 A | 6/1978 | Leveen | |
| 4,119,102 A | 10/1978 | Leveen | |
| 4,140,130 A | 2/1979 | Storm | |
| 4,154,246 A | 5/1979 | Leveen | |
| 4,230,129 A | 10/1980 | Leveen | |
| 4,285,346 A | 8/1981 | Armitage | |
| 4,290,435 A | 9/1981 | Waggott | |
| 4,303,636 A | 12/1981 | Gordon | |
| 4,346,715 A | 8/1982 | Gammell | |
| 4,375,220 A | 3/1983 | Matvias | |
| 4,545,368 A | 10/1985 | Rand et al. | |
| 4,565,200 A | 1/1986 | Cosman | |
| 4,676,258 A | 6/1987 | Inokuchi et al. | |
| 4,709,701 A | 12/1987 | Weber | |
| 4,773,864 A | 9/1988 | Holt | |
| 4,823,791 A | 4/1989 | D'amelio et al. | |
| 4,881,543 A | 11/1989 | Trembly et al. | |
| 4,887,614 A | 12/1989 | Shirakami et al. | |
| 4,955,884 A | 9/1990 | Grossi et al. | |
| 4,962,761 A | 10/1990 | Golden | |
| 5,000,753 A | 3/1991 | Hagen et al. | |
| 5,003,991 A | 4/1991 | Takayama et al. | |
| 5,007,908 A | 4/1991 | Rydell | |
| 5,010,897 A | 4/1991 | Leveen | |
| 5,099,756 A | 3/1992 | Franconi et al. | |
| 5,151,101 A | 9/1992 | Grossi et al. | |
| 5,190,517 A | 3/1993 | Zieve et al. | |
| 5,190,541 A | 3/1993 | Abele et al. | |
| 5,234,004 A | 8/1993 | Hascoet et al. | |
| 5,257,451 A | 11/1993 | Edwards et al. | |
| 5,273,535 A | 12/1993 | Edwards et al. | |
| 5,275,162 A | 1/1994 | Edwards et al. | |
| 5,282,797 A | 2/1994 | Chess | |
| 5,293,863 A | 3/1994 | Zhu et al. | |
| 5,293,869 A | 3/1994 | Edwards et al. | |
| 5,309,910 A | 5/1994 | Edwards et al. | |
| 5,313,943 A | 5/1994 | Houser et al. | |
| 5,314,466 A | 5/1994 | Stern et al. | |
| 5,322,503 A | 6/1994 | Desai | |
| 5,328,467 A | 7/1994 | Edwards et al. | |
| 5,334,193 A | 8/1994 | Nardella | |
| 5,342,357 A | 8/1994 | Nardella | |
| 5,348,554 A | 9/1994 | Imran et al. | |
| 5,363,861 A | 11/1994 | Edwards et al. | |
| 5,366,490 A | 11/1994 | Edwards et al. | |
| 5,368,592 A | 11/1994 | Stern et al. | |
| 5,370,675 A * | 12/1994 | Edwards ............... | A61B 18/00 606/32 |
| 5,370,678 A | 12/1994 | Edwards et al. | |
| 5,383,917 A | 1/1995 | Desai et al. | |
| 5,385,544 A | 1/1995 | Edwards et al. | |
| 5,398,683 A | 3/1995 | Edwards et al. | |
| 5,403,311 A | 4/1995 | Abele et al. | |
| 5,409,453 A | 4/1995 | Lundquist et al. | |
| 5,423,807 A | 6/1995 | Milder | |
| 5,423,808 A | 6/1995 | Edwards et al. | |
| 5,423,811 A | 6/1995 | Imran et al. | |
| 5,433,708 A | 7/1995 | Nichols et al. | |
| 5,435,805 A | 7/1995 | Edwards et al. | |
| 5,437,662 A | 8/1995 | Nardella | |
| 5,454,782 A | 10/1995 | Perkins | |
| 5,456,662 A | 10/1995 | Edwards et al. | |
| 5,458,596 A | 10/1995 | Lax et al. | |
| 5,458,597 A | 10/1995 | Edwards et al. | |
| 5,462,521 A | 10/1995 | Brucker et al. | |
| 5,470,308 A | 11/1995 | Edwards et al. | |
| 5,470,309 A | 11/1995 | Edwards et al. | |
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,505,730 A | 4/1996 | Edwards | |
| 5,507,743 A | 4/1996 | Edwards et al. | |
| 5,509,419 A | 4/1996 | Edwards et al. | |
| 5,514,130 A | 5/1996 | Baker | |
| 5,514,131 A | 5/1996 | Edwards et al. | |
| 5,531,677 A | 7/1996 | Lundquist et al. | |
| 5,536,267 A | 7/1996 | Edwards et al. | |
| 5,540,655 A | 7/1996 | Edwards et al. | |
| 5,542,915 A | 8/1996 | Edwards et al. | |
| 5,542,916 A | 8/1996 | Hirsch et al. | |
| 5,542,928 A | 8/1996 | Evans et al. | |
| 5,545,161 A | 8/1996 | Imran | |
| 5,545,171 A | 8/1996 | Sharkey et al. | |
| 5,545,193 A | 8/1996 | Fleischman et al. | |
| 5,546,267 A | 8/1996 | Frederiksen et al. | |
| 5,549,108 A | 8/1996 | Edwards et al. | |
| 5,549,644 A | 8/1996 | Lundquist et al. | |
| 5,554,110 A | 9/1996 | Edwards et al. | |
| 5,556,377 A | 9/1996 | Rosen et al. | |
| 5,558,672 A | 9/1996 | Edwards et al. | |
| 5,558,673 A | 9/1996 | Edwards et al. | |
| 5,560,358 A | 10/1996 | Arnold et al. | |
| 5,562,703 A | 10/1996 | Desai | |
| 5,582,610 A | 12/1996 | Grossi et al. | |
| 5,599,345 A | 2/1997 | Edwards et al. | |
| 5,662,680 A | 9/1997 | Desai | |
| 5,672,173 A | 9/1997 | Gough et al. | |
| 5,672,174 A | 9/1997 | Gough et al. | |
| 5,683,384 A * | 11/1997 | Gough ............... | A61B 18/1477 606/33 |
| 5,728,143 A | 3/1998 | Gough et al. | |
| 5,759,162 A | 6/1998 | Oppelt et al. | |
| 5,782,827 A | 7/1998 | Gough et al. | |
| 5,810,804 A | 9/1998 | Gough et al. | |
| 5,827,276 A | 10/1998 | Leveen et al. | |
| 5,849,011 A | 12/1998 | Jones et al. | |
| 5,911,036 A | 6/1999 | Wright et al. | |
| 5,921,982 A * | 7/1999 | Lesh ................... | A61B 18/1492 606/41 |
| 5,935,123 A | 8/1999 | Edwards et al. | |
| 5,979,453 A | 11/1999 | Savage et al. | |
| 6,002,968 A | 12/1999 | Edwards | |
| 6,016,452 A * | 1/2000 | Kasevich ............ | A61B 18/1206 606/41 |
| 6,036,689 A | 3/2000 | Tu et al. | |
| 6,050,992 A | 4/2000 | Nichols | |
| 6,066,139 A | 5/2000 | Ryan et al. | |
| 6,071,280 A | 6/2000 | Edwards et al. | |
| 6,190,383 B1 | 2/2001 | Schmaltz et al. | |
| 6,212,433 B1 | 4/2001 | Behl | |
| 6,217,518 B1 | 4/2001 | Holdaway et al. | |
| 6,221,071 B1 | 4/2001 | Sherry et al. | |
| 6,254,601 B1 | 7/2001 | Burbank et al. | |
| 6,312,429 B1 | 11/2001 | Burbank et al. | |
| 6,355,033 B1 | 3/2002 | Moorman et al. | |
| 6,468,273 B1 | 10/2002 | Leveen et al. | |
| 6,497,704 B2 | 12/2002 | Ein | |
| 6,575,967 B1 | 6/2003 | Leveen et al. | |
| 6,575,969 B1 | 6/2003 | Rittman et al. | |
| 6,699,243 B2 | 3/2004 | West et al. | |
| 6,743,226 B2 | 6/2004 | Cosman et al. | |
| 6,837,887 B2 | 1/2005 | Woloszko et al. | |
| 6,840,935 B2 | 1/2005 | Lee | |
| 6,974,455 B2 * | 12/2005 | Garabedian ........ | A61B 18/1482 606/41 |
| 7,416,549 B2 | 8/2008 | Young et al. | |
| 7,419,487 B2 | 9/2008 | Johnson et al. | |
| 8,080,009 B2 | 12/2011 | Lee et al. | |
| 8,512,330 B2 | 8/2013 | Epstein et al. | |
| 8,512,333 B2 | 8/2013 | Epstein et al. | |

(56) References Cited

U.S. PATENT DOCUMENTS

| | | | |
|---|---|---|---|
| 9,510,898 B2 | 12/2016 | Epstein et al. | |
| 9,662,166 B2 | 5/2017 | Lee et al. | |
| 9,861,426 B2 | 1/2018 | Epstein et al. | |
| 2003/0125729 A1 | 7/2003 | Hooven et al. | |
| 2003/0130711 A1 | 7/2003 | Pearson et al. | |
| 2003/0199868 A1 | 10/2003 | Desai et al. | |
| 2004/0215182 A1 | 10/2004 | Lee | |
| 2004/0254572 A1 | 12/2004 | Mcintyre et al. | |
| 2005/0107781 A1 | 5/2005 | Ostrovsky et al. | |
| 2005/0149013 A1 | 7/2005 | Lee | |
| 2006/0189972 A1 | 8/2006 | Grossman | |
| 2007/0006215 A1 | 1/2007 | Epstein et al. | |
| 2007/0016183 A1 | 1/2007 | Lee et al. | |
| 2009/0099544 A1 | 4/2009 | Munrow et al. | |
| 2009/0221998 A1 | 9/2009 | Epstein et al. | |
| 2010/0305439 A1 | 12/2010 | Shai et al. | |
| 2011/0230874 A1 | 9/2011 | Epstein et al. | |
| 2012/0165813 A1 | 6/2012 | Lee et al. | |
| 2015/0066003 A1 | 3/2015 | Epstein et al. | |
| 2015/0066020 A1 | 3/2015 | Epstein et al. | |
| 2017/0296256 A9 | 10/2017 | Epstein et al. | |
| 2018/0125566 A1 | 5/2018 | Epstein et al. | |

FOREIGN PATENT DOCUMENTS

| | | |
|---|---|---|
| WO | WO 2007/005830 | 1/2007 |
| WO | WO 2010/099481 | 9/2010 |
| WO | WO 2012/129447 | 9/2012 |

\* cited by examiner

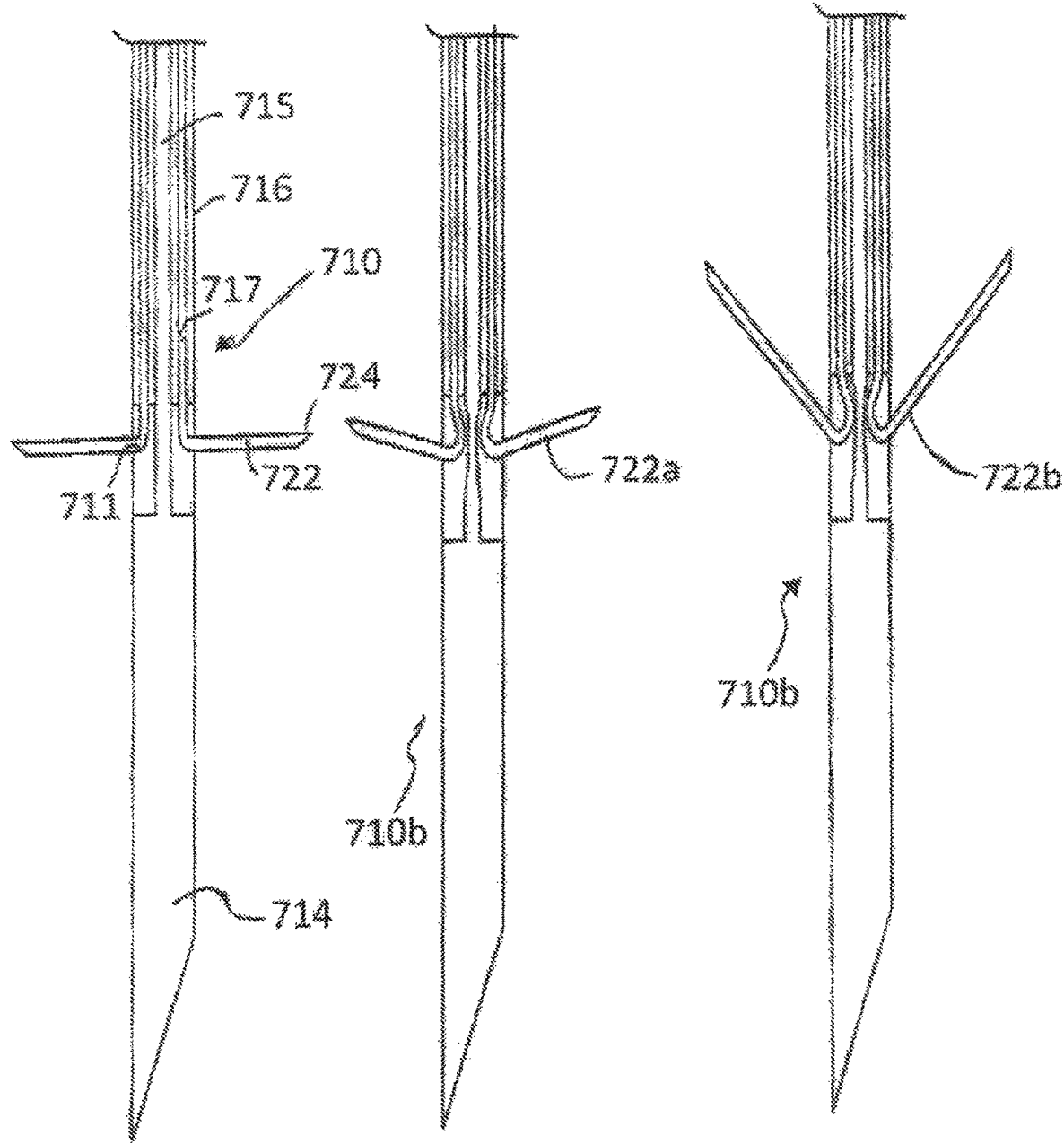

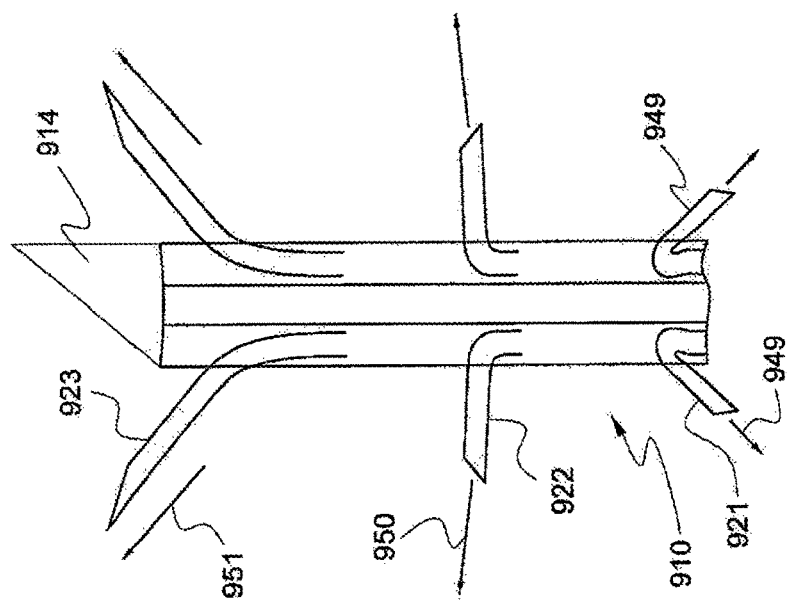
Figure 22
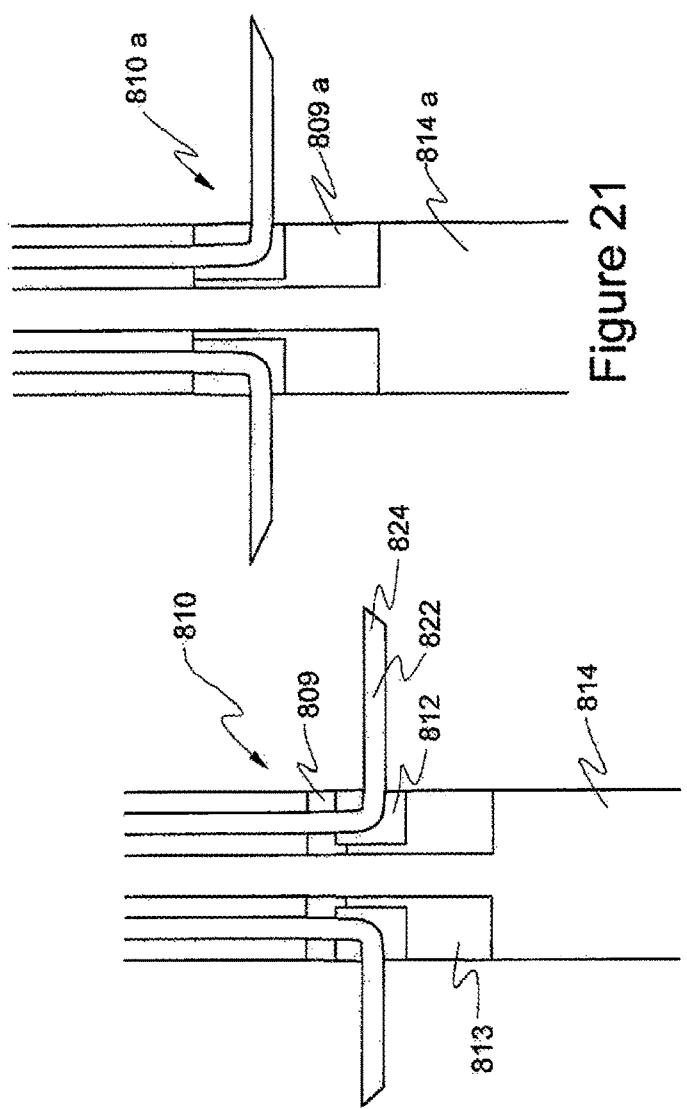
Figure 21
Figure 20

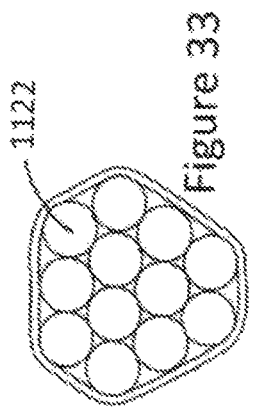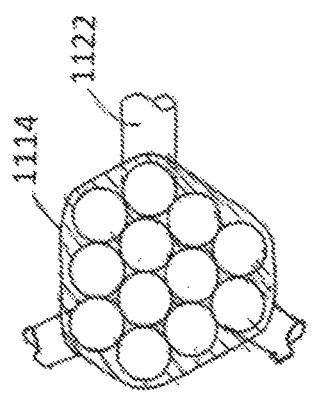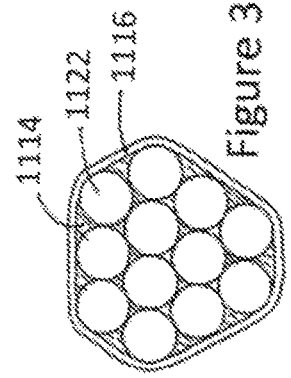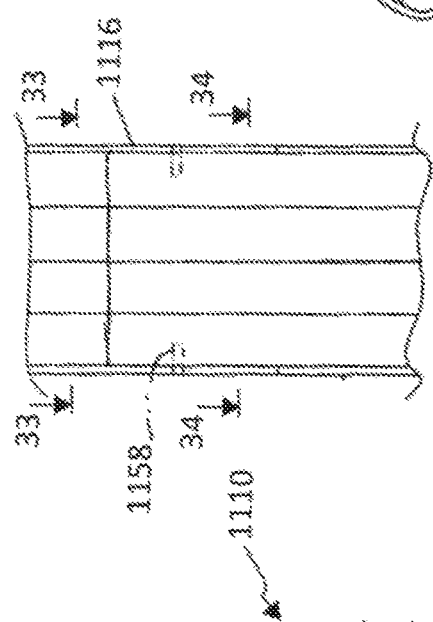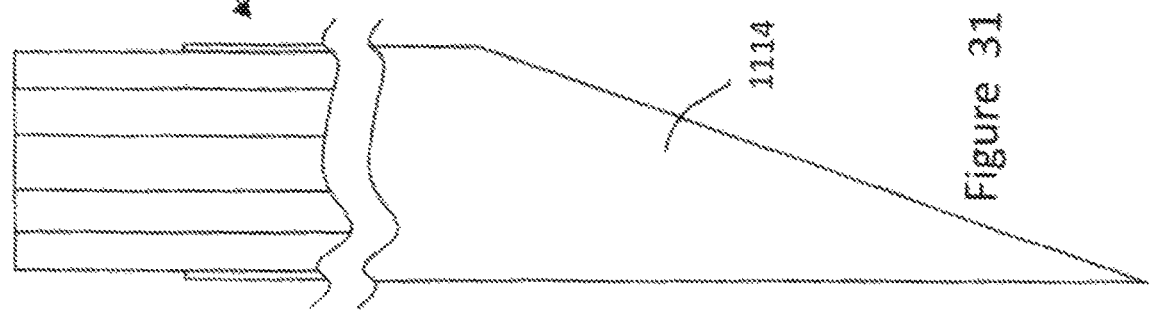

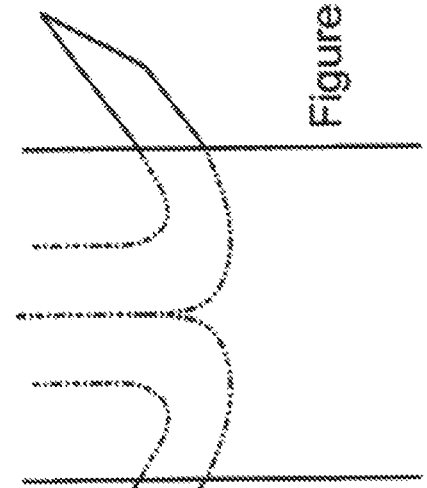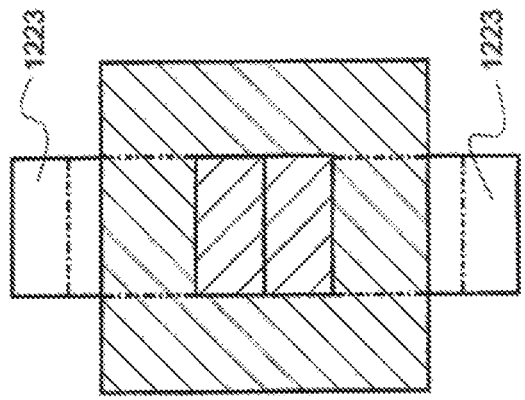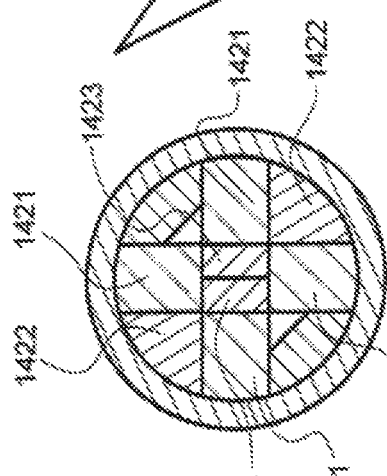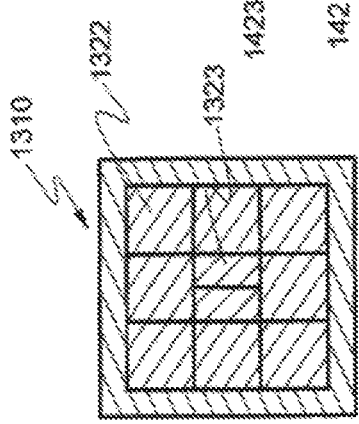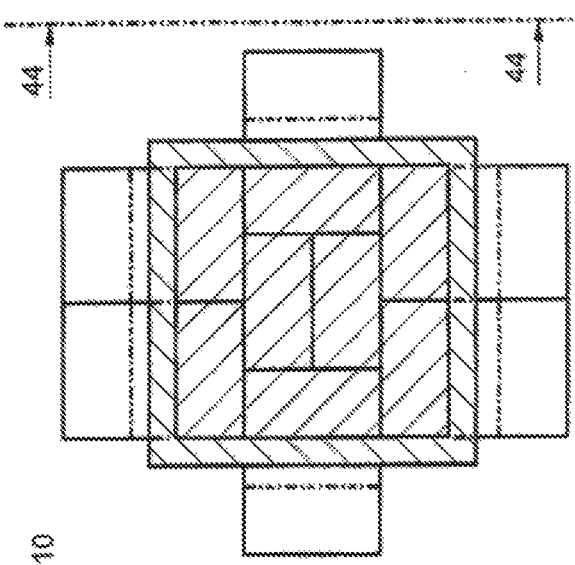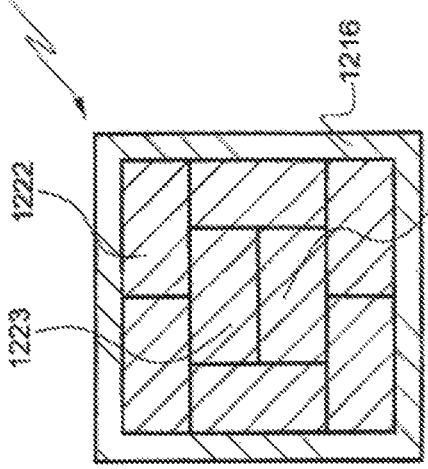

RADIO FREQUENCY ABLATION DEVICE FOR THE DESTRUCTION OF TISSUE MASSES

This application is a continuation of U.S. patent application Ser. No. 13/323,722, now U.S. Pat. No. 9,662,166, filed on Dec. 12, 2011, entitled, RADIO FREQUENCY ABLATION DEVICE FOR THE DESTRUCTION OF TISSUE MASSES, which is a continuation of U.S. patent application Ser. No. 11/173,928, now U.S. Pat. No. 8,080,009, filed on Jul. 1, 2005, entitled, RADIO FREQUENCY ABLATION DEVICE FOR THE DESTRUCTION OF TISSUE MASSES, the disclosures of which is incorporated herein by reference.

BACKGROUND

In the United States, approximately 230,000 women have hysterectomies annually. The primary reason for the performance of these hysterectomies is the existence of substantial symptoms associated with uterine fibroids. In the United States alone, there are more than six million women with uterine fibroid symptoms that prefer to suffer, rather than endure the risks and inconveniences associated with surgery, especially a major surgery that results in infertility. Outside of the United States, the situation is much the same, with millions of women suffering with fibroids in need of a safe alternative to hysterectomy.

Recently, another treatment option (uterine artery embolization) has been introduced. Generally, this procedure involves embolization of the arteries which feed the urine fibroid. This results in cutting off the blood supply to the fibroid and the shrinkage of the fibroid over time. However, the unacceptably high rate of complications severely limits its appeal to patients.

Myomectomy, which generally involves the surgical removal of the fibroid through the use of classical surgical procedures, is another treatment option. However, due to its rate of complications and long recovery time, this option is also not very appealing to patients. Typical complications involve risk of infection, relatively severe postsurgical pain, damage to the uterus and other risks normally associated with such types of surgery. Moreover, such damage to the uterus may be relatively subtle and may only come to light when the uterus begins to swell during pregnancy and ruptures at a weak point created during the surgery, resulting in loss of the fetus.

Still another alternative to treat the discomfort associated with uterine fibroids is the removal of the endometrium which lines the uterus. However, this procedure also results in infertility.

In an attempt to address these issues, an RF ablation probe of the type used to treat tumors in the human liver by hyperthermia has been successfully demonstrated to substantially shrink or eliminate uterine fibroids.

See, for example, U.S. Pat. No. 6,840,935 issued to Lee on Jan. 11, 2005, the disclosure of which is incorporated herein by reference. In that patent a method for treating pelvic tumors, such as uterine leiomyomata, includes inserting an ablation apparatus into the pelvic region and positioning the ablation apparatus either proximate to or into a pelvic tumor.

The method further includes using a laparoscope and an imaging device, such as an ultrasound machine, to confirm the location of the pelvic tumor and placement of the ablation apparatus. An ablation apparatus with multiple needles or deployable arms that are inserted into the pelvic tumor is disclosed. The method involves delivering electromagnetic energy or other energy through the ablation apparatus to the tumor to induce hyperthermia and tumor ablation.

The particular device disclosed for ablating the tumor in U.S. Pat. No. 6,840,935 is of the type disclosed in U.S. Pat. No. 5,728,143, issued to Gough et al. on Mar. 17, 1998. Generally, that device comprises a plurality of resilient springy RF ablation antennae or electrodes which, importantly, are preformed with a curved configuration which they assume after exiting a sharp trocar-tipped catheter. Generally, as the antennae exit the trocar tip, they advance long curved paths (extending along a range of different paths in various portions of the tumor to be ablated) which are defined by their preformed springy shapes. The deployed antennae with their particular preformed shapes thus define an ablation volume. Various shape ablation volumes may be defined by varying the configuration of the curves which are preformed into the various springy antennae. Such devices are manufactured by Rita Medical Systems of Mountain View, Calif. Generally, such devices work by the antennae assuming their pre-formed configuration as they emerge from the trocar tip.

SUMMARY OF THE INVENTION

In accordance with the invention, it has been observed that difficulties are sometimes encountered in using such prior art curved electrode ablation systems. More particularly, it has been observed in accordance with the invention that fibroid tissues tend to be somewhat more difficult to pierce compared to other types of tumors and that this accounts for the problems encountered. To a limited extent, the difficulty of piercing the fibroid with the antennae may be mitigated by advancing very small increments of the ablation antennae into the fibroid, applying radiation to the antennae to induce hyperthermia and degrade the physical integrity of the tissue surrounding the antennae. The antennae may then be advanced into the somewhat deteriorated tissue and the application of radiation to the antennae continued to enlarge the physically deteriorated regions of the tumor, and, after a time, further advancing the antennae.

While this iterative advancement of the antennae, punctuated by relatively long periods of time during which advancement cannot be implemented, requiring the physician to wait for the desired degree of deterioration of the tissue into which the antennae will next be advanced, will work to effectively and minimally-invasively ablate the tumor, the procedure is time-consuming compared to a procedure in which antennae may be fully deployed and radiation applied to a large volume of the tumor during a single application or limited number of applications of RF energy.

Accordingly, while the above procedure has seen some commercial implementation, the time necessary for the procedure has made it relatively expensive and thus it is not available to many individuals. Moreover, the skill required for the performance of the procedure is relatively high, and thus few doctors are able to perform the procedure. Moreover, proliferation of this approach is not likely in view of the steep learning curve and the small number of individuals competent to perform this procedure. Nevertheless, in accordance with the invention, it is believed that a quick and easy to implement RF ablation procedure would be very attractive to doctors and patients in view of the low risk of complications and the relatively lower likelihood, under a typically encountered set of circumstances, that the uterus will be damaged and fail during a subsequent pregnancy.

In spite of the fact that this method for treating uterine fibroids has been known for a number of years, no such alternative apparatus has been devised for improving the procedure.

In accordance with the invention, the inventive ablation element comprises an elongated cannula having a proximal end and a distal end. The cannula defines an internal lumen within the cannula and a cannula axis. A plurality of conductors are contained within the lumen. Each of the conductors has a proximal end proximate the proximal end of the cannula, and a distal end proximate the distal end of the cannula. A plurality of ablation stylets each has a proximal end and a distal end, and each is coupled at the respective proximal end of the stylet to the distal end of a respective conductor. The stylets comprise a deflectable material. The conductors together with their respective stylets are mounted for axial movement. A trocar point is defined proximate the distal end of the cannula. A deflection surface is positioned between the trocar point and the proximal end of the cannula. The deflection surface is configured and positioned to deflect, in response to axial movement of the stylets in a direction from the proximate end of the cannula to the distal end of the cannula, at least some of the stylets laterally with respect to the cannula axis in different directions along substantially straight paths. The straight stylet is deflected from its straight trocar axis parallel path by the curved trocar guide surface in the mandrel over a curved or rounded counter surface directly adjacent to the curved track. This arrangement provides for a maximum in the amount of stylet deflection in a given volume. In accordance with the invention the stylet may only be contacted by guiding surfaces at two or three points to reduce friction. This rapid and abrupt change in direction is needed to limit the cross sectional area of the delivery cannula that carries the stylets and penetrates into the target tissue. The design of the pathway, the opposing curved surface over which the stylet is bent, the spring characteristics of the stylet and the level and orientation of the point on the stylet all have to be adjusted to minimize friction and yet maximize the degree of deflection that can be achieved. The stylet may be very easy to bend and take the curve easily but of insufficient structural integrity to penetrate the target tissue. The stylet may be very rigid but then unable to make the needed deflection into the tissue. If the bend is made but the friction of deployment is too great the instrument might be difficult to use. Even within one tip mandrel a variety of angles may be desired. This is achieved by variously adjusting the curvature of the "paths" in the mandrel and the proximity of the rounded counter surface over which the stylet is bent to the depth of the curved path. When these stylets exit the mandrel into the tissue they define an ablation volume in the target tissue.

Each of the conductors may be selected from the group consisting of electrical conductors, radio frequency conductors, microwave conductors and optical conductors.

Each of the conductors may be integral with its respective ablation stylet. The solid contents of the lumen consist essentially of the conductors. Each of the stylets may be configured to assume a substantially straight configuration in the absence of external forces.

An ablation element further comprises a finger operated slider, pliers activator or motor member or members or other drive system coupled to the conductors to drive axial movement of the stylets in directions from the proximal end of the cannula to the distal end of the cannula, and from the distal end of the cannula to the proximal end of the cannula through a plurality of positions. The trocar point may be defined at the distal end of a trocar member. The trocar member has an outside surface. The cannula has an outside surface. The trocar member has a proximal end secured proximate to the distal end of the elongated cannula. The outside surface of the cannula and the outside surface of the trocar point define a trocar surface.

The deflection surface comprises a number of ramps defined proximate the proximal end of the trocar point. The distal ends of the stylets are positionable proximate to the ramps and within the trocar surface.

In the preferred embodiment, the conductors and the stylets are electrical conductors. Each of the stylets may be configured to assume a substantially straight configuration in the absence of external forces.

The deflection surface comprises a plurality of channels guiding the distal ends of the stylets to the ramps. The cannula may be secured to the trocar member with the outside surface of the cannula proximate to the outside surface of the trocar member.

An ablation element also comprises an anchor mounted for movement between an internal position disposed within the trocar surface and an anchoring position extending laterally from the trocar surface through points external to the lumen. A drive member is disposed within the lumen and coupled to the anchor to drive the anchor between the internal position and the anchoring position.

The anchor comprises at least two pointed members mounted for movement in directions which have vector components which extend away from the axis of the cannula and away from each other.

The pointed members extend in a direction with a vector component that extends in a direction opposite to the direction in which the trocar point extends. The conductors bear against each other at least along a portion of their length within the cannula.

The conductors are driven by a drive mechanism which allows the conductors to move independently. The conductors have a length, a width and a thickness, the width being greater than the thickness, and terminate in a point oriented to allow deflection by the deflection surface. The conductors extend in different directions when they exit the deflection surface and extend to a variable extent.

The anchor members, alone may be utilized as electrodes for ablation of tissue. Alternatively, the anchor members may be used simultaneously in combination with the tip electrodes. When used together, this could create a larger ablation volume within the target tissue as compared to the ablation volume created when only the tip electrodes have ablative energy applied to them. When used alone, the ablation energy applied to the anchor members alone may be used in anatomic situations where retrograde deployment of electrodes is desired or even required.

The electrodes may be used in a monopolar fashion with the ablation stylets excited with RF energy and a return electrode being applied usually in the form a conductive pad in contact with a remote surface on the patient. Excitation may be applied in a bipolar fashion where one set of electrodes, such as the tip electrodes could serve as negative electrodes and the anchor electrodes may serve as the positive electrodes and create an ablation volume between the two sets of electrodes.

Separately, a cauterizing RF current can be supplied to the tip mandrel by the RF generator. Surgical RF generators may be separated into generators that are designed for ablation, or the controlled heating of tissue to bring about cellular death without charring or desiccation, and electrosurgical RF generators that are well known in the art for the ability to char and desiccate tissue for the purpose of coagulation of vessels to control bleeding, and cutting of tissue for rapid tissue dissection. Electrosurgical generators used for cauterization tend to be of higher power and current than those used for ablation. In accordance with the invention, cauterizing is delivered to the metal trocar tip of the cannula as the cannula is withdrawn to provide for cauterization of the track as the cannula is withdrawn. Traditional RF ablation generators apply a "track ablate" mode of somewhat higher wattage of ablation energy for this purpose, but do not approximate the energy delivered to the tissue by electrosurgical generators known in the art, as is employed in the present invention.

The conductors are driven by a drive circuit which varies the amount of energy supplied to the stylets and/or the length of the stylets and/or the length of time during which power is supplied to the stylets and/or the angular orientation of the ablation element.

The parameters of stylet length, stylet power, stylet actuation time and/or angular orientation may be controlled by a computer in response to a computer program having an input comprising feedback information from the tissue area being operated on and/or a preset program.

An anchor or anchors are mounted for movement between an internal position disposed within the trocar surface and an anchoring position extending laterally from the trocar surface through points external of the lumen. A drive member is disposed within the lumen and coupled to the anchor to drive the anchor between the internal position and the anchoring position. The anchor comprises one two or more pointed members mounted for movement in a direction which has vector components which extend away from the axis or the cannula and in the case of two anchors, also extend away from each other.

The front end is a trocar point defined at the distal end of the trocar member.

The anchors may be deployed in response to rotary motion. The anchors are deployed by bearing against a deflection surface. The anchors are made of a springy material which may assume a curved configuration when not subjected to external forces.

As compared to a conventional hysterectomy, the present invention is thus directed to a device for the treatment of uterine fibroids and other tissue masses that meets the needs of women by conserving the uterus and reducing recovery time from 6 to 8 weeks to 3 to 10 days.

BRIEF DESCRIPTION OF THE DRAWINGS

FIG. 17 is another alternative embodiment of the inventive trocar with stylus emerging substantially vertically to the trocar point;

FIG. 18 is yet another alternative embodiment of the inventive trocar with stylus emerging in a slightly retrograde fashion relative to the direction of advancement of trocar point;

FIG. 19 is still yet another alternative embodiment of the inventive trocar with stylus emerging in a highly retrograde fashion relative to the direction of advancement of trocar point;

FIG. 20 is a front view of the delivery surface of the embodiment of the inventive trocar comprising a sandwich of a proximal plastic angular member, a metal mandrel and a distal plastic annular member;

FIG. 21 is a front view of the embodiment of the inventive trocar comprising a single plastic annular member with a meal guide member;

FIG. 22 is a schematic view of an embodiment of the invention illustrating the different directions of stylet deployment;

FIG. 31 is a front view illustrating the structure of yet still another alternative trocar constructed in accordance with the present invention;

FIG. 32 is cross-sectional view of the juncture between the trocar point and the cannula;

FIG. 33 is a cross-sectional view along lines 33-33 of FIG. 32;

FIG. 34 is cross-sectional view along lines 34-34 of FIG. 32;

FIG. 35 is a cross-sectional view of the position and direction of bending of a stylet in the embodiment of FIG. 32;

FIG. 36 is cross-sectional view along lines 36-36 of FIG. 35;

FIG. 41 is a cross-sectional view illustrating the trocar of the present invention with relatively flat electrodes;

FIG. 42 is a cross-sectional view illustrating the employment of stylets in the embodiment of FIG. 41;

FIG. 43 is a cross-sectional view illustrating the employment of anchors in the embodiment of FIG. 41;

FIG. 44 is a cross-sectional view illustrating the position of the deployed anchor;

FIG. 45 is a cross-sectional view of an ablation trocar with square shaped stylets;

FIG. 46 is a cross-sectional view of a trocar with irregular shaped stylets.

DETAILED DESCRIPTION OF THE BEST MODE

Figure 1:
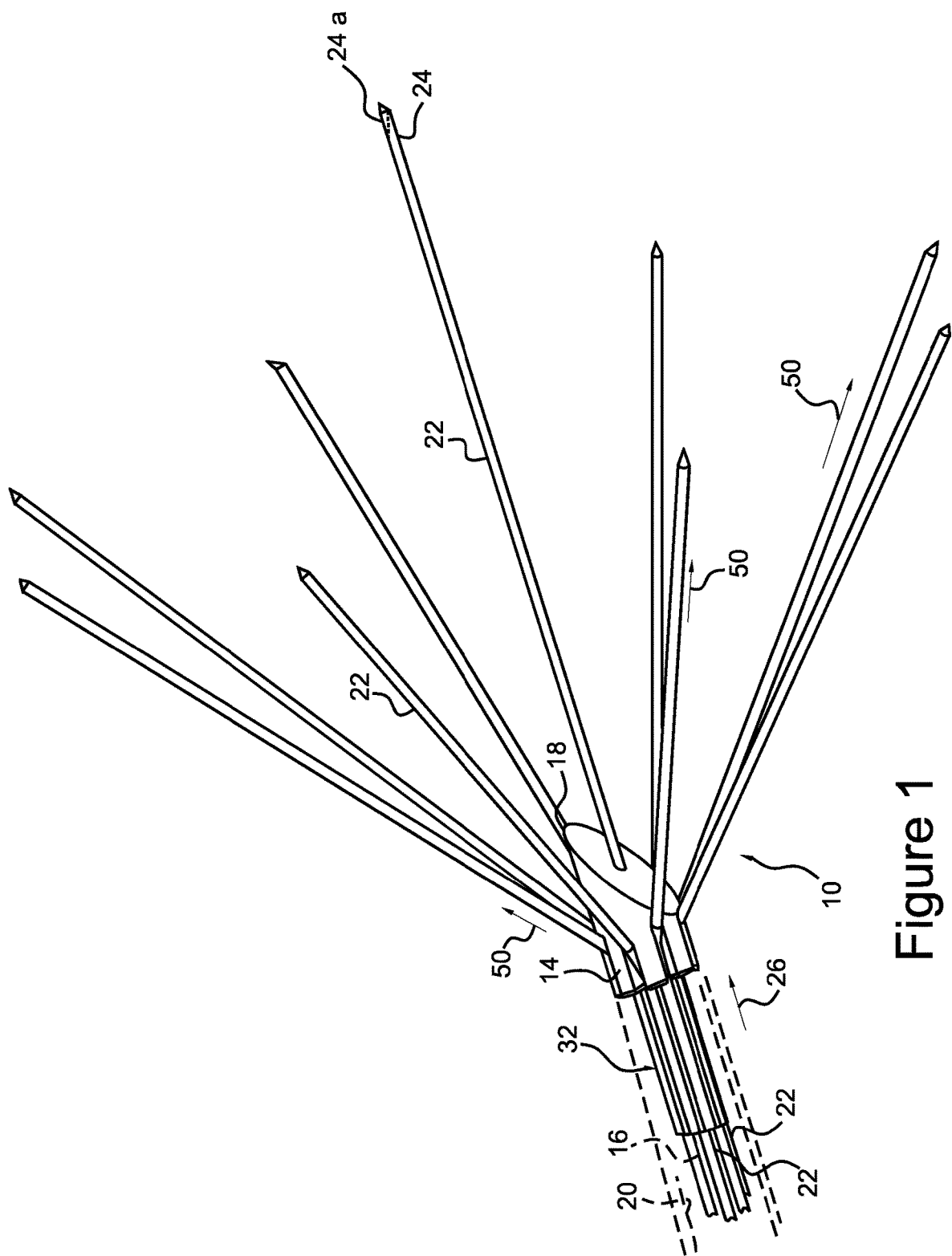
FIG. 1 is a perspective view of the multiple antenna ablation device of the invention.

Hyperthermal treatment of tissues of the human body is well established. It has been used for hemostasis, destruction or ablation of tissues, tightening or shrinkage of various tissues and for other purposes. In accordance with the invention this and other methods for destruction of tissue may also be deployed, such as the delivery of laser light at high intensity levels, the use of conventional resistive heating elements, and other energy delivery devices which can be deployed within tissue. The source of heating may be varied and includes but is not limited to radiant heating, electrical current, radio frequency or microwaves, ultrasound and others.

A number of methodologies utilize radio frequency heating of tissues for ablation or shrinkage by the application of the energy to the tissues through specialized delivery devices. These devices often have electrodes or antenna that are placed into, or onto, the tissue to be treated. Some of these systems incorporate monitors that can provide feedback to the operator, or the device system itself, as to the progress of the treatment. This may be in the form of a readout of the temperature of various parts of the tissue, how much and over what time the energy is being delivered, or a feedback control system to the energy generator itself to control the delivery of energy to the tissue. Often the desired result is the heating of the tissue as quickly and uniformly as possible to destroy the target tissue without charring of target tissue or necrosis of tissue which is not being targeted. Charring of target tissue interferes with a uniform and predictable heating of the target tissue.

In accordance with the invention energy delivery devices are provided which are adapted to the destruction of target tissue at the site where the electrodes are located. Accordingly, the operator can deliver the treatment safely and effectively. One such target tissue for the devices of the present invention is a uterine fibroid. A physician may wish to place an energy delivery device to deliver energy such as radiofrequency current (RF) into the mass of the fibroid in order to cause it to shrink and become less symptomatic to the patient.

A uterine fibroma is a benign muscle tumor which forms in the wall of the female uterus. The tissue is highly vascular, firm and difficult to penetrate even with a sharpened needle. Where ablation of the tumor is to be preformed, it is important for the physician operator to carefully place the ablation stylets (for example radiofrequency electrodes) in the correct positions within the fibroid prior to applying ablative energy.

Furthermore, in accordance with the invention, it is recognized that it is useful if the electrodes or their delivery device experience minimal migration in the forward and backward directions during and after the electrode placement process.

In accordance with the invention, a device is provided that allows multiple straight electrodes (i.e. electrodes substantially without curvature) to be pushed into and through the tough fibroid tumor tissue. The straight electrodes have greater column strength and will have superior mechanical advantage over curved electrodes when deployed into this type of tissue and will permit easier, safer and more accurate placement. The straight electrodes are directed into the tissue at a variety of angles by a mandrel-like delivery member which serves as a deflection surface. This delivery mandrel does not impart a permanent shape to the electrode. Rather its action is limited to redirecting the electrode at an appropriate angle. The electrodes can be made of shape memory material such as NiTi.

In addition to the delivery mandrel, an anchor system is provided in accordance with the invention. A number of alternate designs are disclosed herein but the same are described by way of example and other suitable anchor systems may be employed.

The disclosed anchor systems allow the operator to stabilize the delivery device prior to deployment or withdrawal of electrodes, and thus improve electrode placement. The anchors prevent the device from migrating backward when pushing the electrodes into the firm tissue or forward when pulling the electrodes out.

The inventive system contemplates a variety of methods where the operator would apply the anchor, for example prior to electrode placement. Alternately, an anchor or anchors may be deployed after placement of the ablation electrodes. It is also contemplated in accordance with the invention that there are circumstances where anchors might not be applied at all. Likewise, in accordance with the invention it is contemplated that anchoring functions may also be performed by ablation stylets.

Referring to FIG. 1, an ablation trocar 10 incorporating a plurality of delivery mandrel surfaces 12 (FIG. 2) on a trocar point 14 is illustrated. In accordance with the invention, trocar point 14 is mounted on a cannula 16. Cannula 16 may be made of any suitable material, such as plastic, or metal (covered with a plastic insulating layer, to prevent ablative energy from leaking out of the device along the length of the cannula. Trocar point 14 includes a forward piercing edge surface 18. Metal cannulas coated with an insulator are preferred for their strength.

Cannula 16 defines an internal lumen 20 which carries a plurality of stylets 22. Stylets 22 are made of a springy conductive material such as a springy nickel titanium alloy. In accordance with the invention, each of the stylets 22 comprises a long and straight springy wire-like member which may be housed wholly within lumen 20 of cannula 16, as illustrated in phantom lines in FIG. 2. Because the ends of the wire-like stylets 22 are exposed, elements that form in the case of electrically conductive stylets for applying RF energy, 28 at their tips which form stylets 22 after they exit trocar 10, only the stylets 22 apply ablative energy, and thus tissue surrounding cannula 16 is substantially unaffected, except for the trauma caused by passage of the trocar through the tissue. The stylet may be withdrawn back into a tip mandrel 24 and the RF cauterizing energy applied to the tip mandrel alone during withdrawal of trocar 10 following completion of ablation. When it is decided to advance the tip 24 of a stylet into a tissue mass to be subjected to ablation, tip 24 is advanced in the direction of arrow 26. Improved piercing may be obtained by sharpening the tip 24 to form a point 24a, as illustrated in phantom lines in FIG. 1. As tip 24 is advanced, it bears against surface 12, which deflects it as is more fully described below. The result is to cause the stylets 22 to be laterally deflected and assume the configuration illustrated in FIG. 1.

Stylet 22 may be left in the position illustrated in FIG. 1 during withdrawal of the trocar, and may be driven with RF energy or other suitable input during withdrawal to achieve canterization of the elongated wound which formed the path of the trocar.

Figure 2:
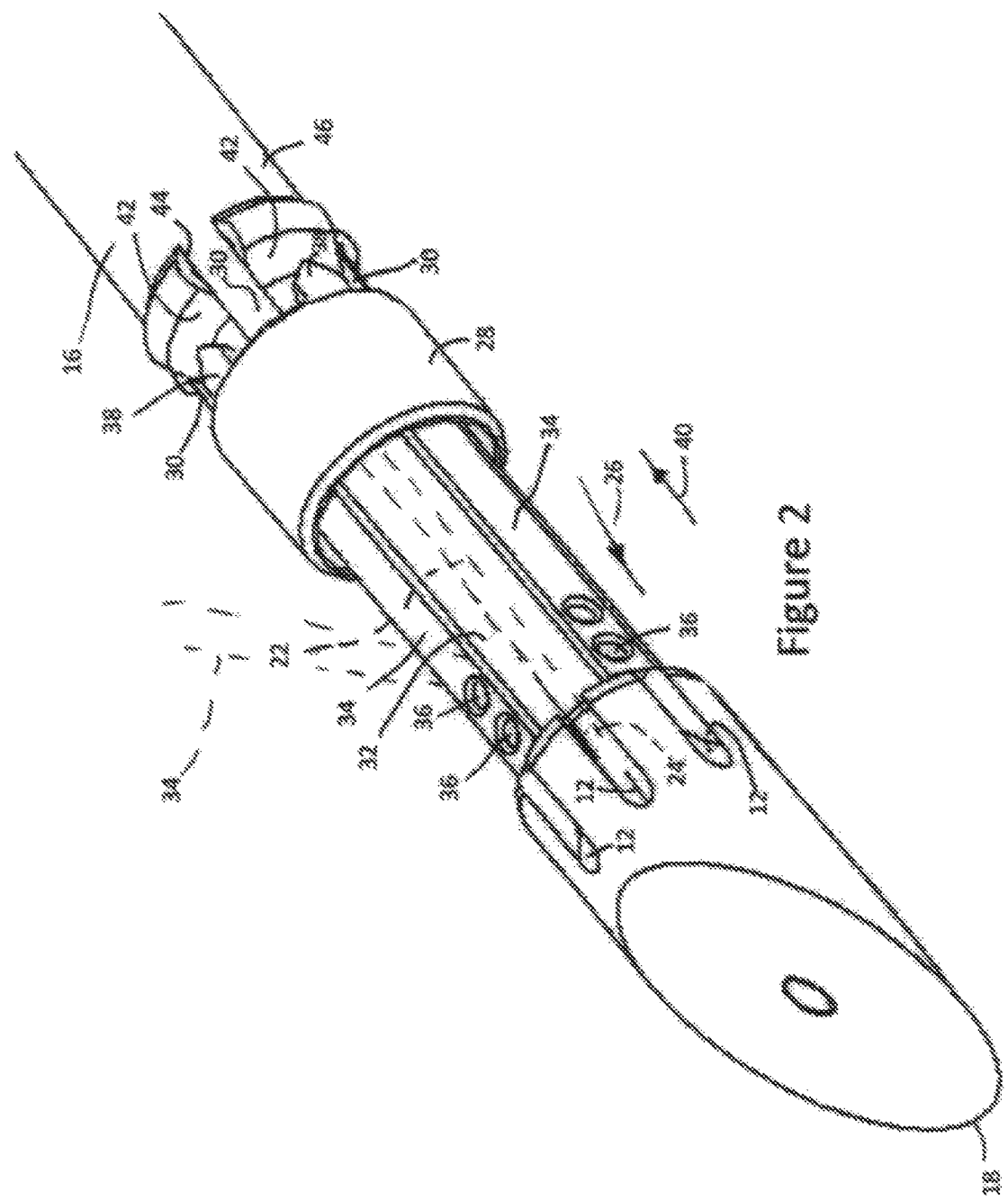
FIG. 2 is a perspective view of a delivery manual with an anchoring system.

Referring to FIG. 2, ablation trocar 10, mounted on cannula 16 includes a collar 28 secured to a plurality of axially oriented ridges 30 disposed around the circumference adjacent cannula 16. Collar 28 is rigidly secured to ridges 30 and is in spaced relationship to substantially concentric inner sleeve 32 Inner sleeve 32 is slidably mounted within cannula 16 and is secured to and supports trocar point 14 Inner sleeve 32 may be made of plastic or other flexible material.

A plurality of anchors 34 are secured by numerous means such as fasteners 36 or laser welding to inner sleeve 32. Anchors 34 terminate at points 38 which are sharpened to easily pierce the tissue and thus anchor the trocar. Anchors 34 are disposed in the space between collar 28 and inner sleeve 32, and are adapted to slide in the directions indicated by arrows 26 and 40. Anchors 34 are made of a springy material and except for the influence of collar 28 would assume the position illustrated in phantom lines in FIG. 2.

Cannula 16 also supports and is rigidly connected to a plurality of deflection surfaces 42 against which points 38 bear during the anchoring procedure, as will be described in detail below. Deflection surfaces 42 may be formed on a single annular member which is fitted on to and around the end of cannula 16 and which includes a plurality of arcuate surfaces 44 which bear against and may be glued or otherwise secured to the outer surface 46 of cannula 16.

In accordance with the invention, a wide variety of materials may be used to manufacture the inventive trocar 10. For example, all members may be made of plastic except for the very tip of forward piercing edge surface 18 and stylets 22.

Figure 3:
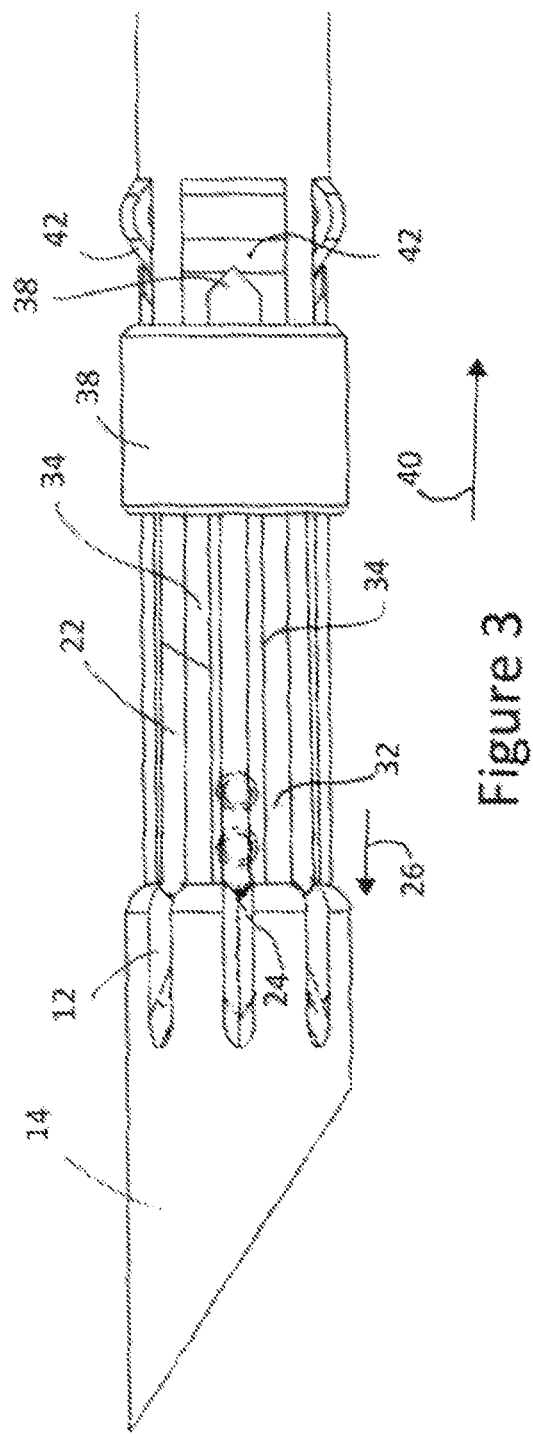
FIG. 3 is a front view of the inventive probe with anchor system of the device illustrating the trocar before deployment of the anchor.

When it is desired to use the inventive ablation trocar 10, for example to ablate a uterine fibroid, trocar 10 is put into the configuration illustrated in FIG. 3. In this position, the points 24 of each of the stylets 22 are not deflected and positioned at the input of the delivery mandrel surfaces 12. Ablation trocar 10 is then advanced, in the case of a uterine fibroid, into the uterus in the manner described in the above-incorporated patent of Lee. Alternatively, the inventive trocar may be inserted through other paths, depending upon the location of the particular fibroid to be destroyed or other factors.

Figure 4:
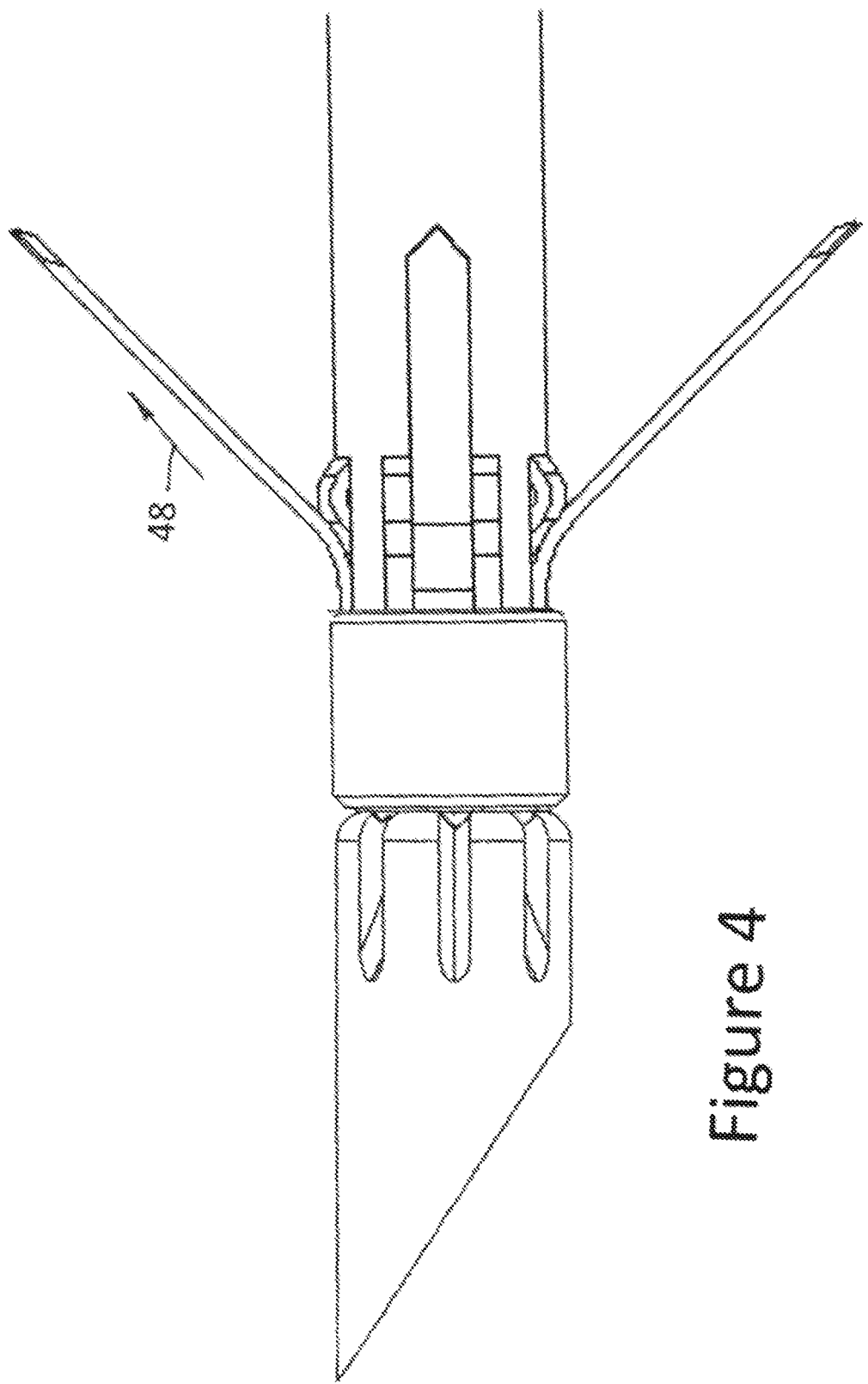
FIG. 4 is a perspective view of the apparatus of the present invention with anchors deployed.

Once the trocar point 14 and those parts of ablation trocar 10 proximate thereto are in position for the deployment of ablation stylets 22, anchoring may be implemented by withdrawal of inner sleeve 32 into cannula 16. As sleeve 32 is withdrawn into cannula 16, it pulls anchors 34 in the direction indicated by arrow 40, pushing anchor points 38 against deflection surfaces 42, causing the flexible resilient anchors 34 to be deflected laterally in the directions illustrated in FIG. 4, under the combined influence of the inner surface of collar 28 and deflection surfaces 42 which induce an outward lateral bend.

In accordance with the present invention it may be desired that the anchors be relatively rigid and strong. Accordingly, in order to achieve the desired amount of bending in such a rigid member, the anchors are of a flat cross-section.

Also in accordance with the invention, the anchors may be made of a conductive material and driven with RF energy to serve as ablation stylets.

As the anchors are advanced with their tips moving in the direction indicated by arrow 48, they pierce the surrounding tissue and thus anchor the trocar point 14 against retrograde motion when stylets 22 are advanced. The stylets are advanced by causing them to move from the position illustrated in FIG. 3 in the directions of arrow 26. This causes them to bear against delivery mandrel surfaces 12, deflecting them laterally and outwardly in the directions indicated by arrows 50 (FIG. 1). This results in the distal end of the trocar 10 taking the configuration illustrated in FIG. 1.

Figure 5:
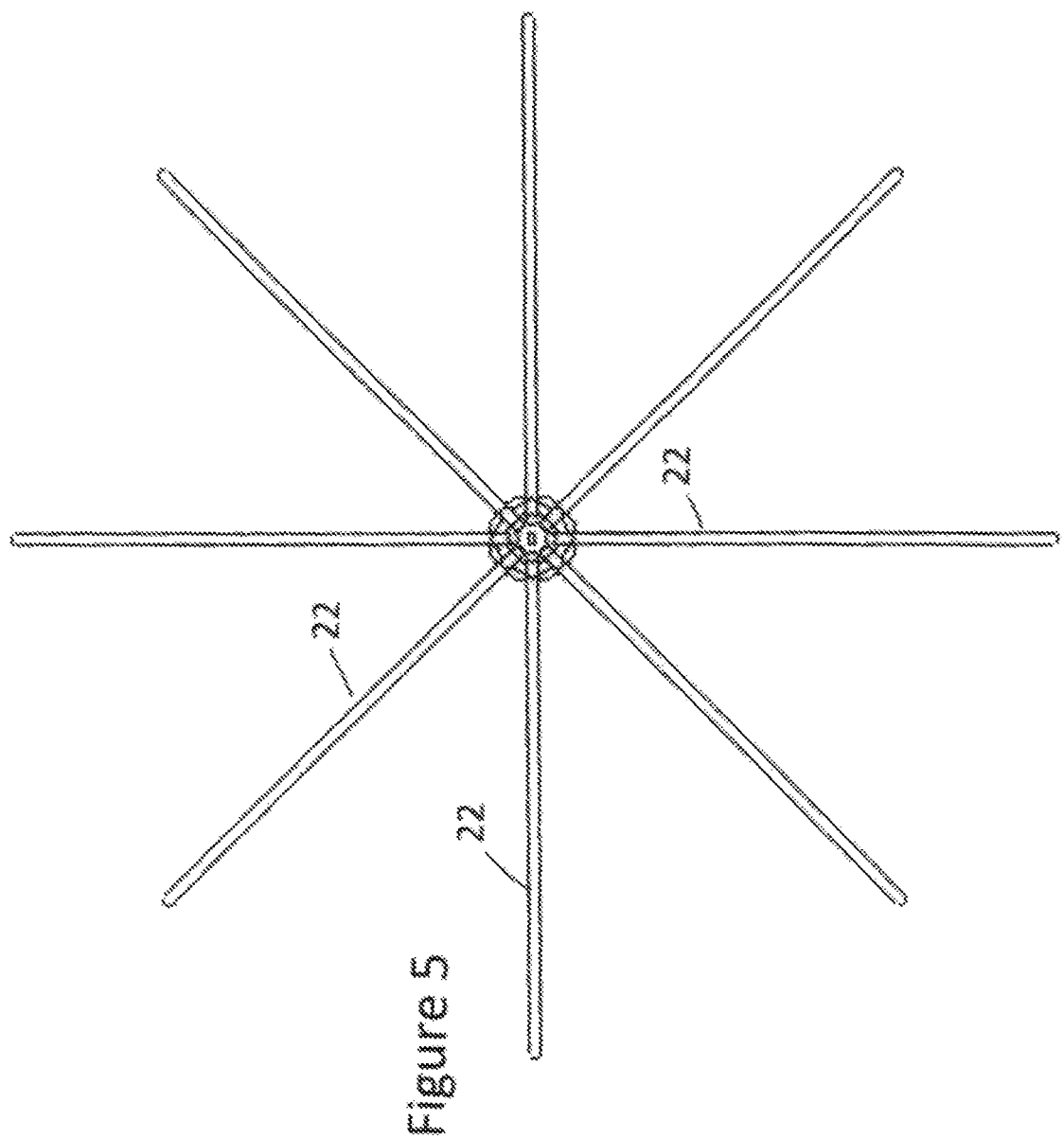
FIG. 5 is a front plan view with nine trocars deployed.

While the arrangement of stylets may be may to form any desired pattern, in the illustrated embodiment, a cone is achieved as can be seen with reference to FIGS. 1 and 5.

If desired, anchors may first be deployed one at a time to minimize unwanted displacement of the distal end of trocar 10. Likewise, if desired, anchors may not be deployed. An implementation of a use of the inventive trocar 10 without the anchors would be promoted by advancing the ends of stylets 22 one at a time, thus minimizing their tendency to displace the trocar.

Moreover, in accordance with the invention, the advancement of stylets singly, in combination or in any desired pattern, as well as the controlled single, multiple or other advance in a pattern for anchors may be controlled by an electronic control circuit, microprocessor computer or any other system, thus simplifying controls on the device held by the physician. Likewise, any desired steering system may be incorporated into the trocar, in addition to or as a substitute for manual manipulation of the uterus during the advancement of the trocar to and through the target tissue.

In accordance with the present invention, the wires which comprise stylets 22 extend from the distal end of trocar 10 to the proximal end of trocar 10, not illustrated, where they may be connected to suitable advancement and retraction mechanisms. Such mechanisms may be of a conventional design. However, in accordance with the invention, the same may be motorized and/or computerized to operate automatically in synchronous or sequential fashion. Also, in accordance with the invention, the patterns of anchor and/or electrode deployment may be varied to achieve any desired effect.

After the stylets 22 have been successfully deployed in the tumor mass to be ablated, RF energy, in the instant example, is applied to the stylets using a signal intensity sufficient to heat target tissue to a sufficiently high temperature to result in hyperthermia and consequent destruction of the target tissue. However, care must be taken not to apply too much energy to the target tissue because charring of the target tissue in a very narrow region surrounding the stylet will create an insulative jacket around the stylet, preventing enough RF energy from passing through and reaching the target tissue beyond the jacket in sufficient quantities to result in ablation of that portion of the target tissue.

Figure 6:
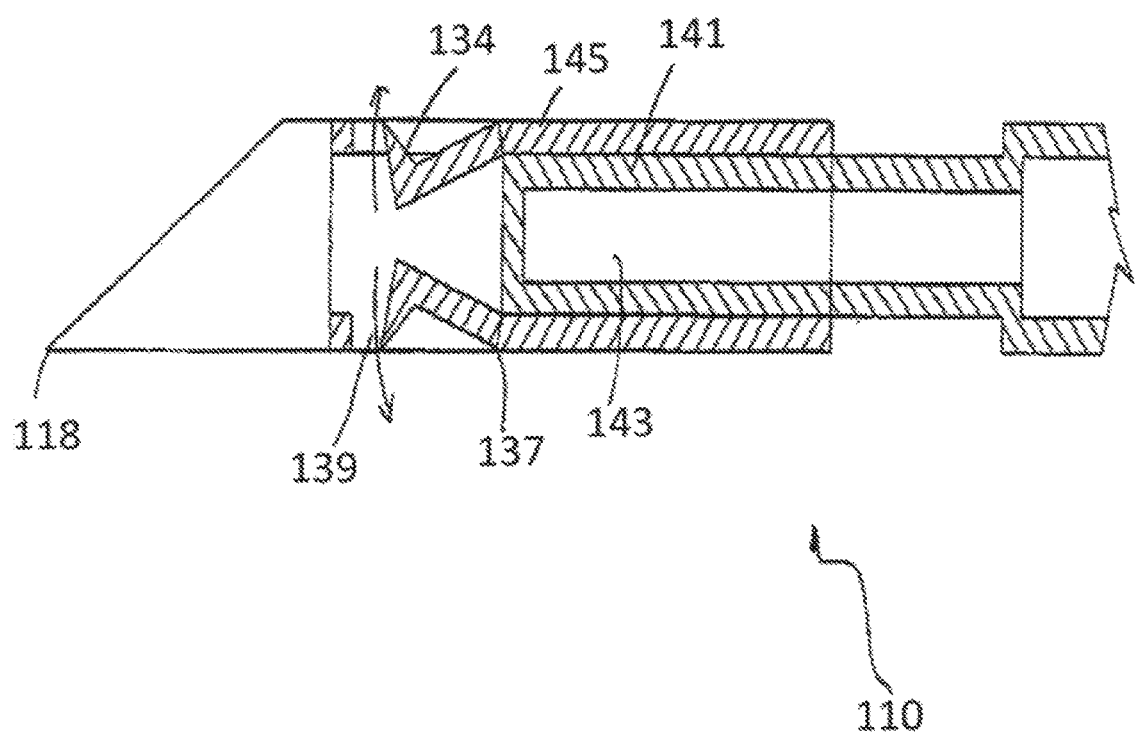
FIG. 6 is a cross-sectional view of an alternative anchoring structure.

Referring to FIG. 6, an alternative anchoring structure for an ablation trocar 110 including ablation electrode structure of the type illustrated in FIGS. 1-5 is shown. The trocar 110 illustrated in FIG. 6 includes a pair of anchors 134 mounted on arms 135 which are mounted for rotation about living hinges 137. Arms 135 rotate in the directions indicated by arrows 139.

Figure 7:
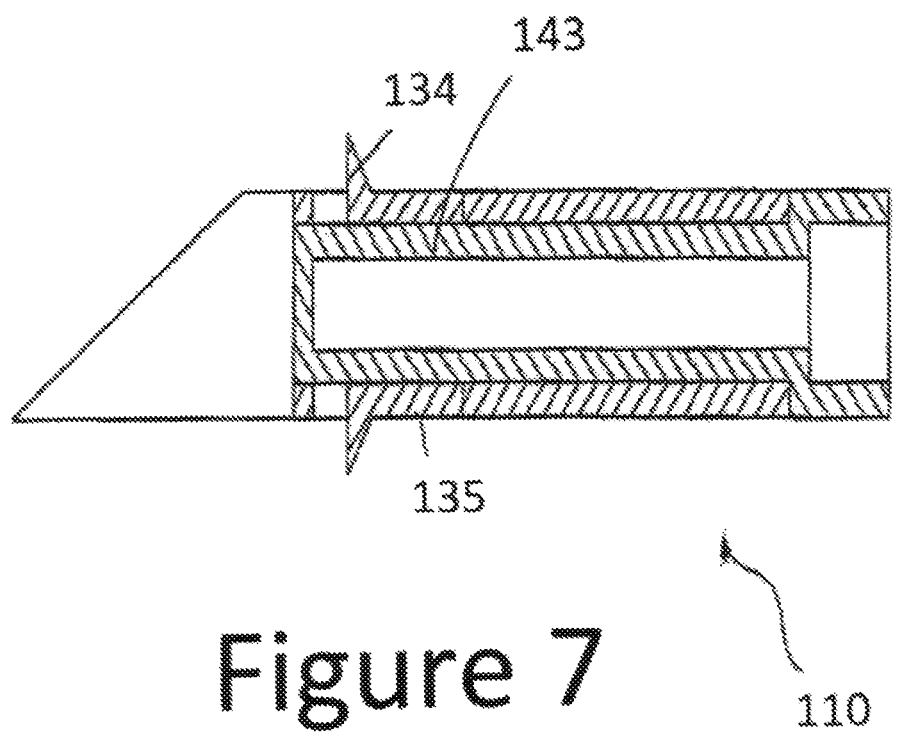
FIG. 7 is a cross-sectional view illustrating the position of the deployed anchors in the embodiment of FIG. 6.

Trocar 110 may be used in the same manner as the trocar illustrated in FIGS. 1-5. After being advanced through the piercing action of forward piercing edge surface 118, anchors may be deployed. When it is desired to deploy the anchors, actuator 141 is advanced in the direction of arrow 143, resulting in the point of trocar 110 taking the position illustrated in FIG. 7.

When the doctor desires to remove the trocar or advance it to another position, actuator 141 is withdrawn to the position illustrated in FIG. 6, causing arms 135 to assume the position illustrated in FIG. 6 on account of the arms 135 resiliently returning to their original position. In accordance with the invention, the anchor may be formed by a plurality, for example, of resilient arms 135 mounted on a tubular member 145. Tubular member 145, resilient arms 135, and anchoring points 134 may be made integral with each other and made of a plastic capable of taking a point.

Figure 8:
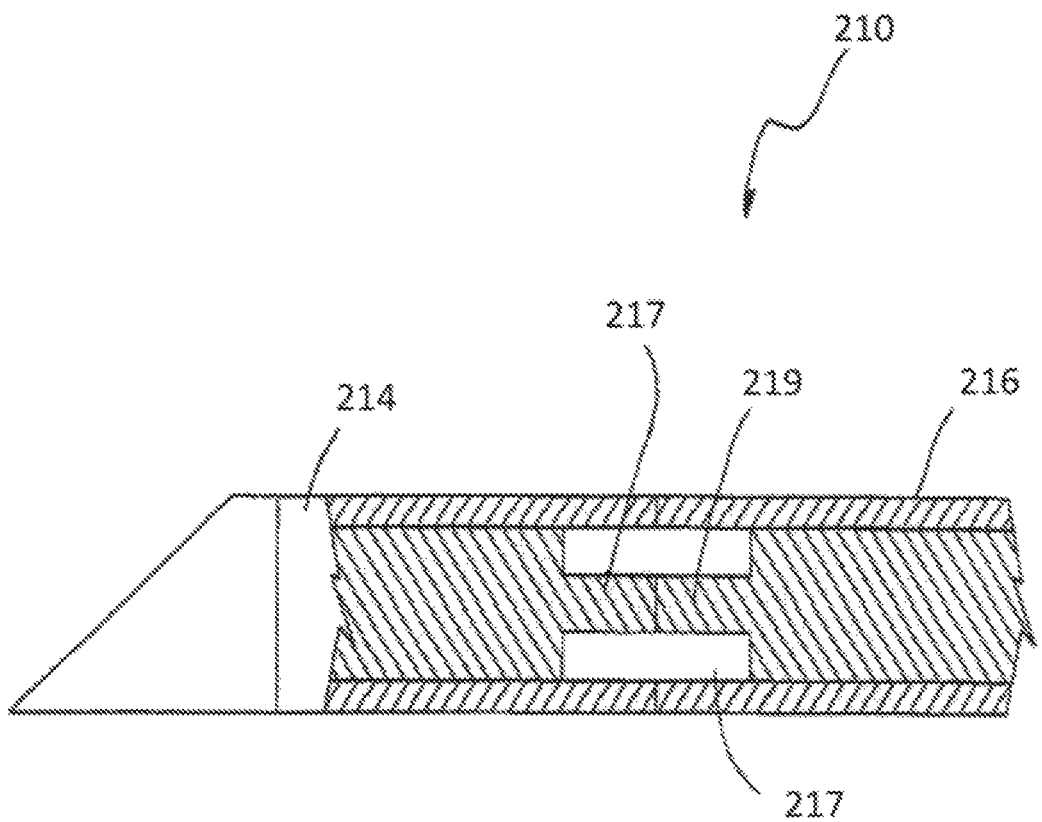
FIG. 8 is a cross-sectional view illustrating another alternative anchoring structure.
Figure 9:
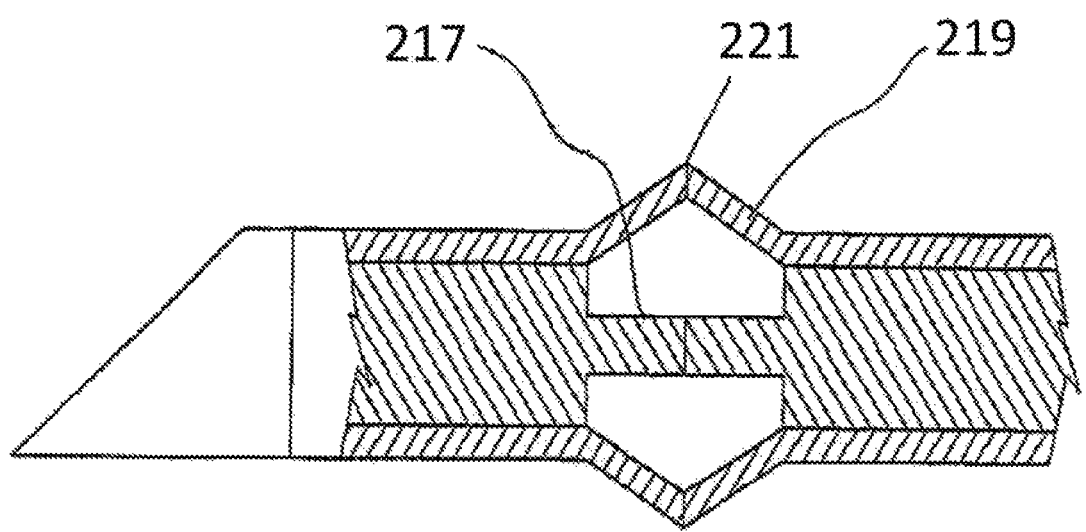
FIG. 9 is a cross-sectional view illustrating the anchoring structure of FIG. 8 after applying force to actuate the anchors.

Still yet another anchoring structure is illustrated in FIG. 8. In ablation trocar 210, cannula 260 includes a plurality of slits 217. By the application of force bringing trocar point 214 closer to cannula 216, the fingers 219 defined between slits 217 may be crimped as illustrated in FIG. 9. The result is the definition of points 221, which will tend to lock into surrounding tissues to anchor trocar 210.

Figure 10:
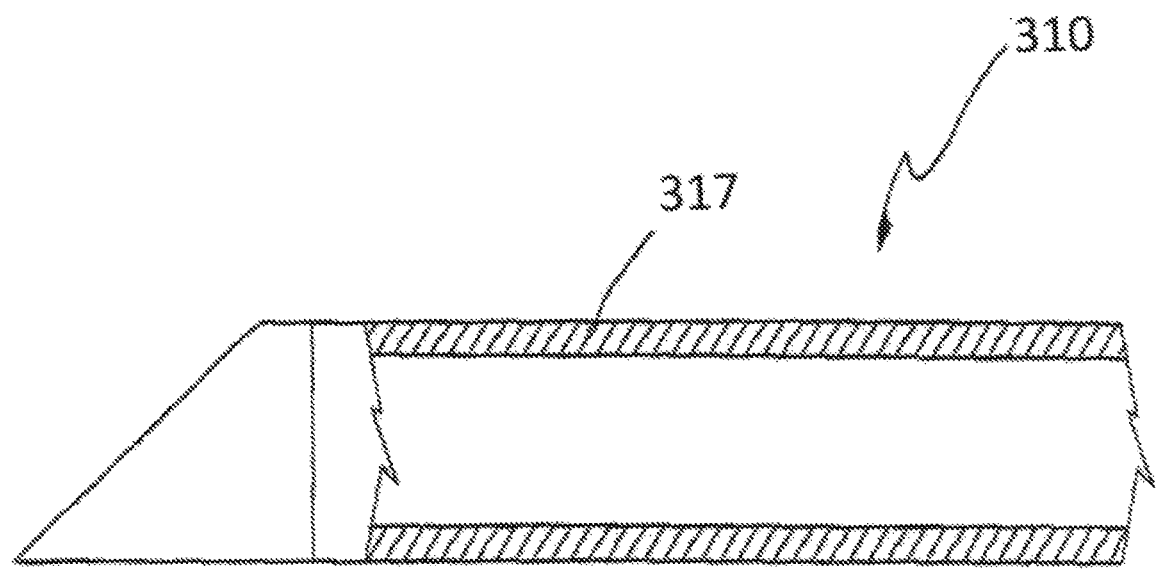
FIG. 10 is a cross-sectional view of yet another alternative anchor structure.
Figure 11:
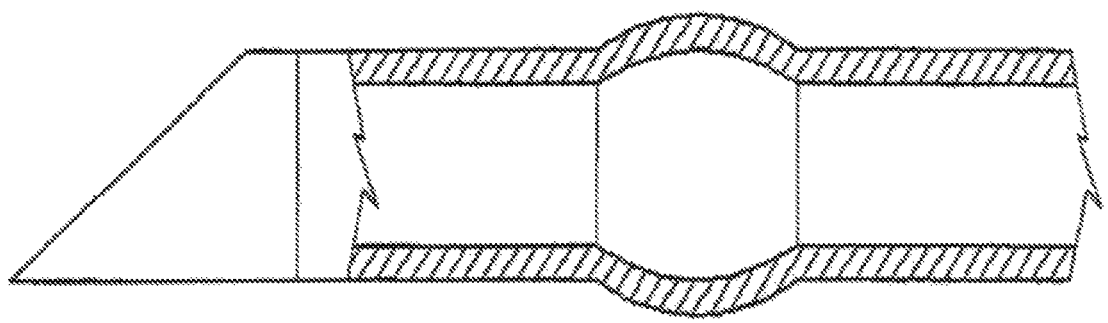
FIG. 11 is a cross-sectional view of the ballooned anchor structure of FIG. 10.

Yet another anchoring structure for a trocar 310 is illustrated in FIG. 10. Here an intermediate section 317 capable of ballooning as illustrated in FIG. 11 is utilized as an anchoring structure.

Figure 12:
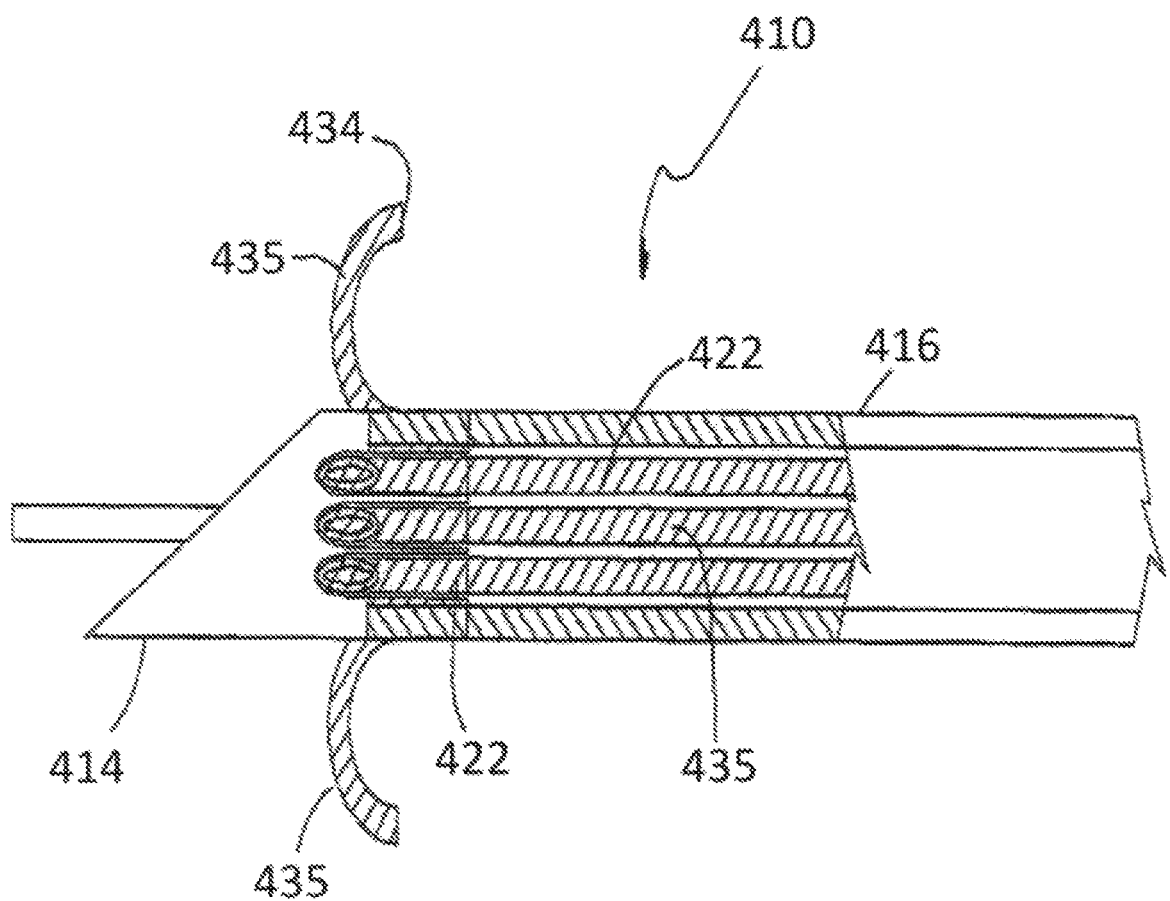
FIG. 12 is a side plan view illustrating a resilient curved configuration anchoring structure for trocars made of springy wire material.

Referring to FIG. 12, a trocar 410 with the yet another anchoring mechanism is illustrated. In this embodiment, anchors 435 are formed of a resilient metal and have points 435. Anchors 434 are preformed with a resilient curved configuration. In other words, anchors 434 are made of a springy wire material which is a delivered in a relatively straight configuration conforming to the path along which the trocar is advanced because they are located in cannula 416. Upon exit from trocar 410, anchors 434 tend to take the illustrated curved configuration, which they springingly return to when not subjected to external forces. The anchors thus extend along and in cannula 416, exiting near the distal point 414 of the trocar. The anchors are advanced from the cannula in the same manner as the ablation electrodes in the embodiment of FIGS. 1-5. In accordance with this embodiment of the invention, stylets 422 (shown in the retracted position in the figure may be advanced out of trocar point 414 in the manner of the embodiment of FIGS. 1-5.

Figure 13:
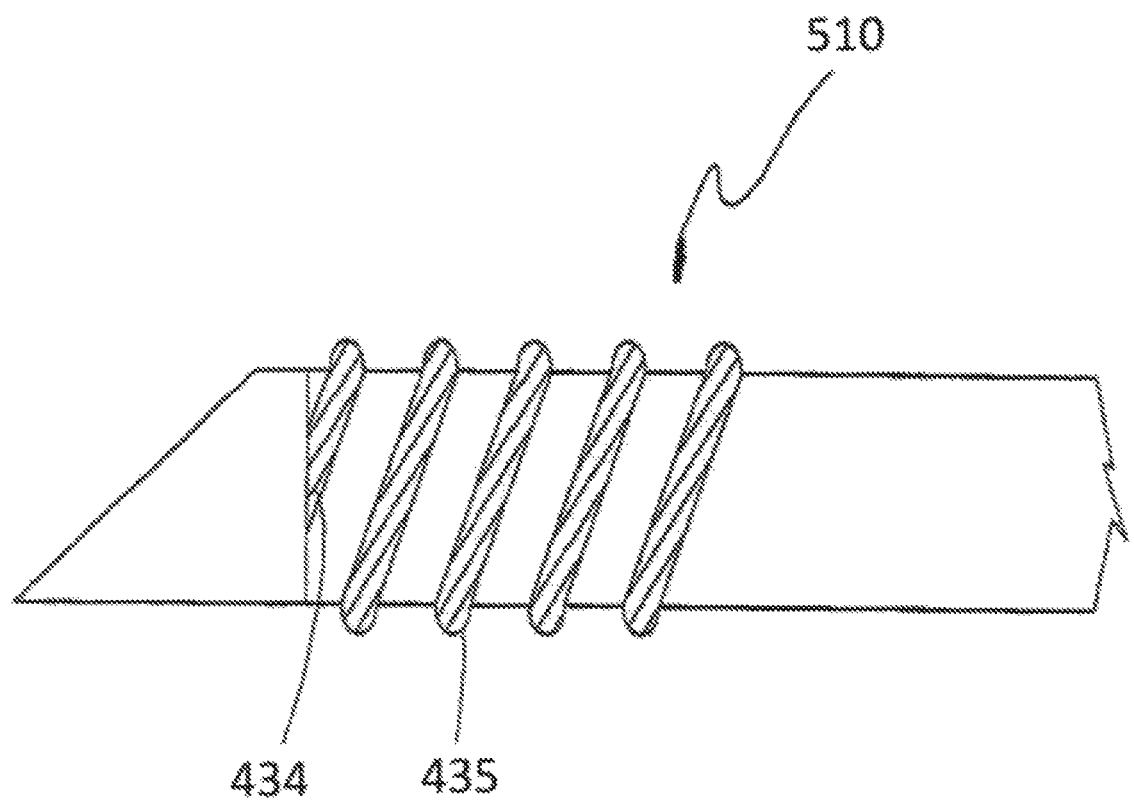
FIG. 13 is a side plan view of a structure with a spiral anchoring device.

Yet another approach is illustrated in FIG. 13, where trocar 510 includes a spiral anchor 435, which may, for example, surround the end of the cannula. Spiral anchor 435 may be rotated to advance anchor point 434 into the tissue adjacent the area to be ablated.

Figure 14:
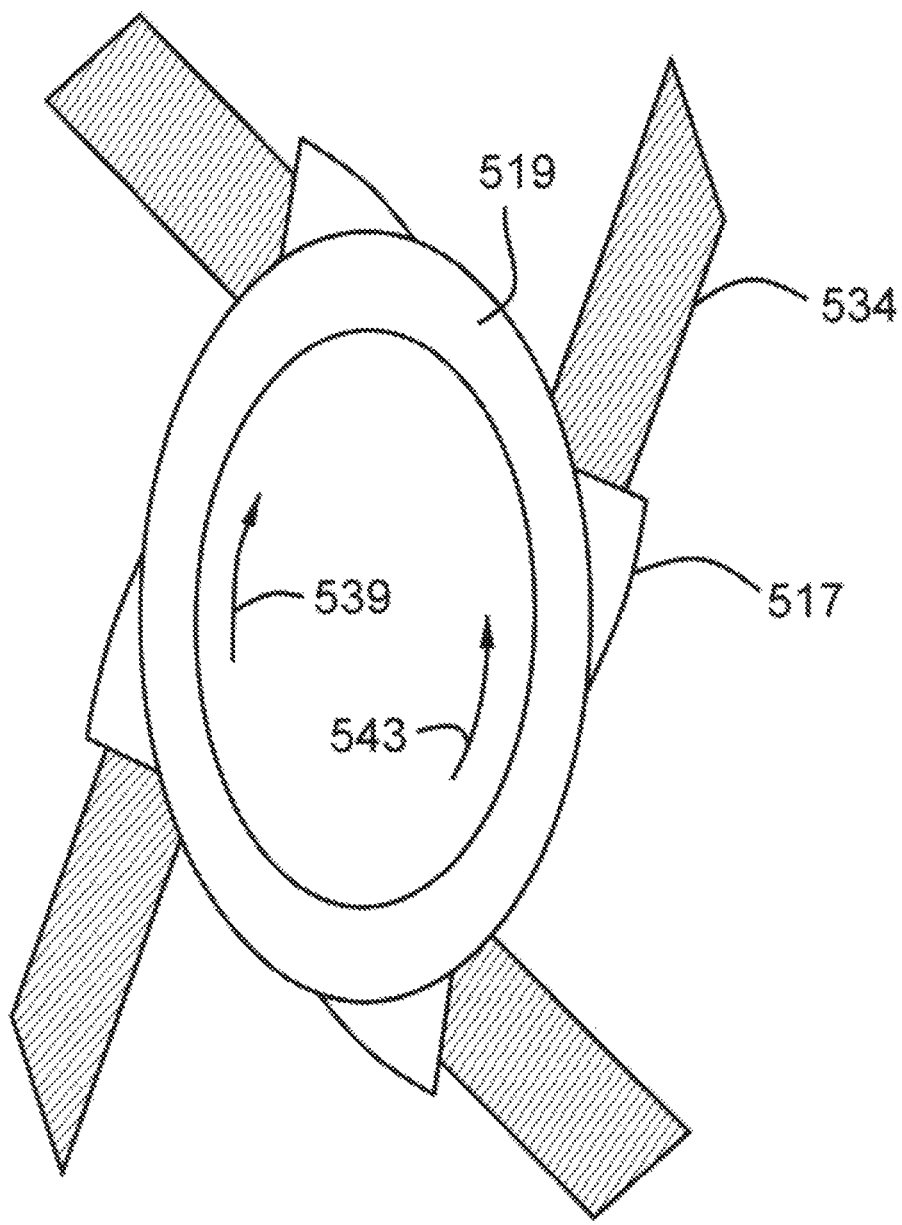
FIG. 14 is a top plan view illustrating a rotatably deployable anchoring structure.
Figure 15:
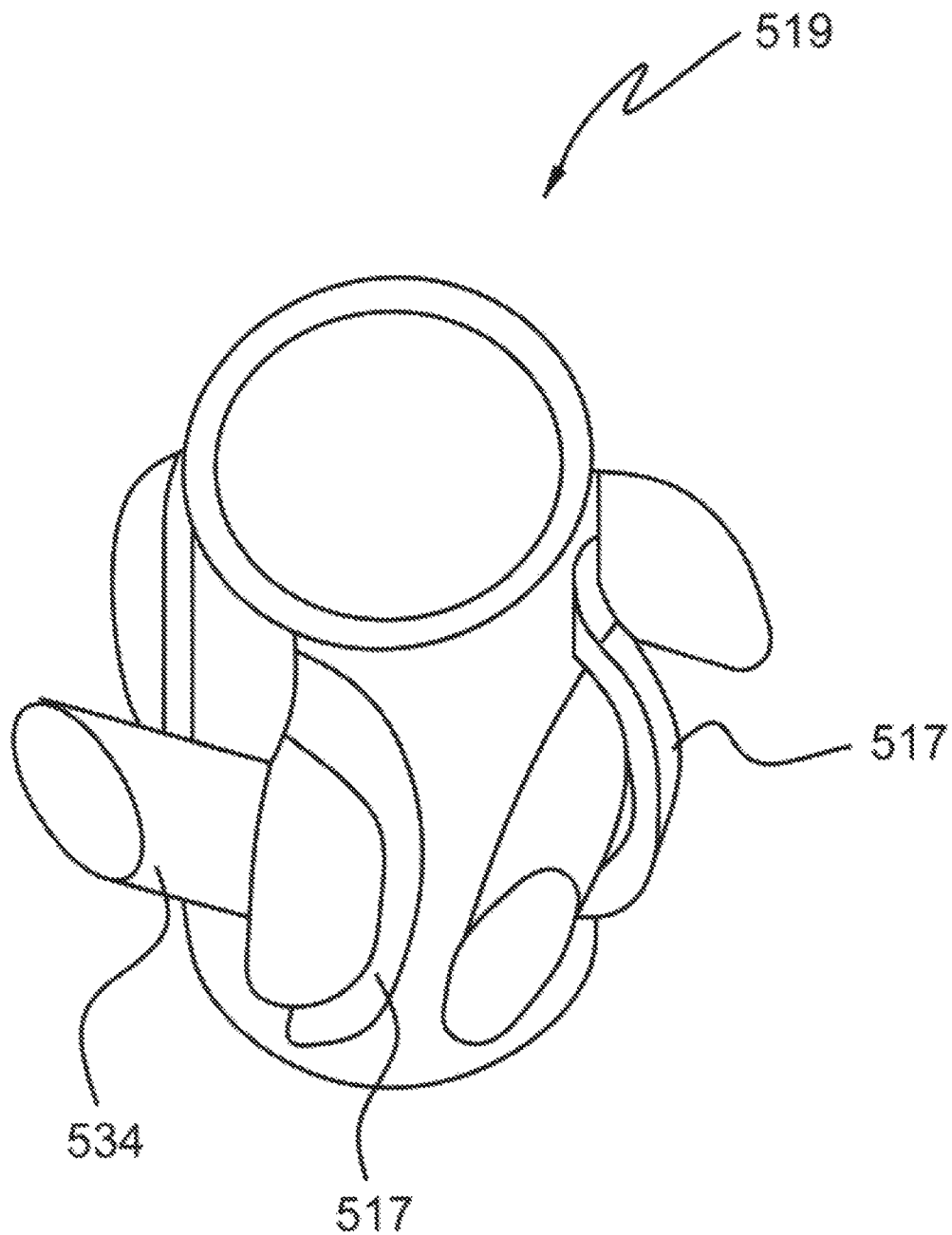
FIG. 15 is a perspective view of the anchoring structure of FIG. 14.

In accordance with the invention, it is also possible to utilized an anchoring structure such as that illustrated in FIGS. 14 and 15. In accordance with this system, the cannula of the trocar incorporates feed-through cowls 517 defined in an anchor housing 519. Anchors 534 are advanced out through cowls 517 by being driven with circumferential motion in the directions indicated by arrow 543. Alternatively, they may be retracted by advancement in the opposite direction indicated by arrow 539.

Figure 16:
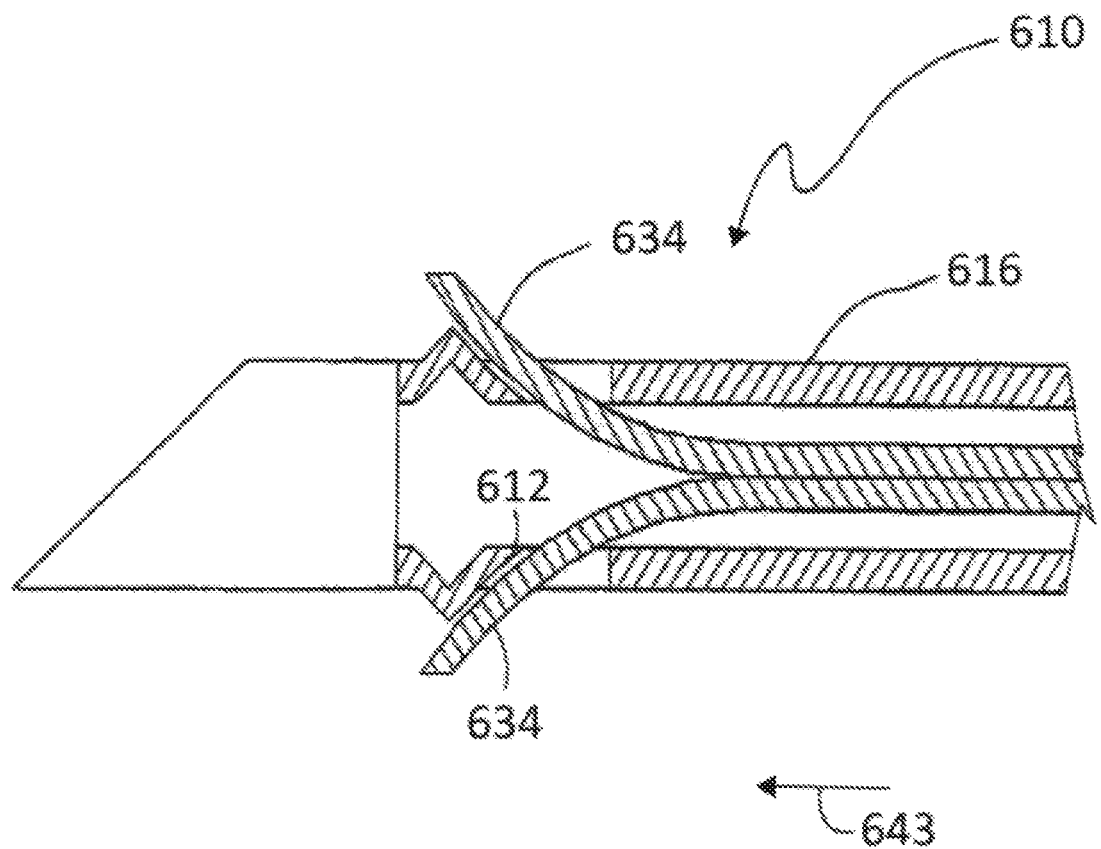
FIG. 16 is a cross-sectional view illustrating structure for deployment of an anchor which extends the entire length of the cannula to a suitable actuation structure.

Referring to FIG. 16, still yet another possibility is the employment in a trocar 610, including a cannula 616, which contains anchors 634 at the end of wire like elements which extend the entire length of the cannula to a suitable actuation structure. Such anchors 634 may be driven in the direction indicated by arrow 643. Anchors 634 are driven out by delivery mandrel surfaces.

It is noted that the various anchoring mechanisms illustrated in FIGS. 6-16 may be used with any of the ablation electrode structures illustrated in the various embodiments of the invention described herein or with similar ablation electrode arrangements.

Turning to FIG. 17, an alternative embodiment of the trocar 710 constructed in accordance with the present invention is illustrated. In accordance with this embodiment, ablation stylet 722, which is an electrode, passes within the walls of the cannula 716 which has a plurality of passages 717, which may be positioned at equal intervals along the circumference of cannula 716 and wholly within the sidewall of cannula 716. Thus, during use, stylets 722, after exiting deflection passages 711 in delivery member 712, pierce the surrounding tissue through the action of points 724. Good physical integrity is achieved by having a metal trocar point 714 secured to the distal end of central axial member 715, which is also metal, which may also be thinned to allow additional volume for the deflection of the ablation electrode. Delivery member 712 may be made of metal to accommodate relatively high degrees of angular deflection by passages 711. Such greater degrees of angular deflection and a thinned central axial member are illustrated in FIG. 18, which has a stylet 722*a* with a slightly rearward motion being angled toward the proximal and of the trocar. FIG. 19 illustrates an even more retrograde path for stylet 722*b*.

As illustrated in FIG. 20, the delivery surface of this embodiment of the inventive trocar 810 may comprise a sandwich of a proximal plastic angular member 809, a metal mandrel 812 and a distal plastic annular member 813. Distal plastic annular member 813, in turn, provides support for trocar point 814.

Alternatively, as illustrated in FIG. 21, another embodiment of the inventive trocar 810*a* may comprise a single plastic annular member 809*a* with a metal guide member 812*a*. It is noted that the angle of point 824 is oriented to provide for easy sliding motion of stylet 822 in delivery passage 811.

In accordance with one embodiment of the invention, as illustrated schematically in FIG. 22, a trocar 910 may include rearwardly and proximally extending stylets, comprising, for example, radiofrequency or RF ablation electrodes 921. Substantially vertically exiting electrodes 922 are also included in this embodiment of trocar 910. Finally, the same trocar 910 also includes distally extending RF electrodes 923. Radiofrequency ablation electrodes 921, 922 and 923 are advanced in the directions of arrows 949, 950 and 951, respectively, during deployment of the electrode into target tissue.

In connection with the embodiment illustrated schematically in FIG. 22, it is noted that stylets 921 may be deployed before stylets 922 and 923, because they are facing in the direction opposite that of the trocar point 914 and will thus effectively act to anchor trocar 910.

The provision of multiple electrodes extending in different directions, as schematically illustrated in FIG. 22 may be used to define the shapes of various ablation volumes.

Further variations in ablation volume may be achieved by varying (for example, in accordance with the present invention by computer) the extent to which stylets 921-923 are extended from the distal end of trocar 910.

Figure 23:
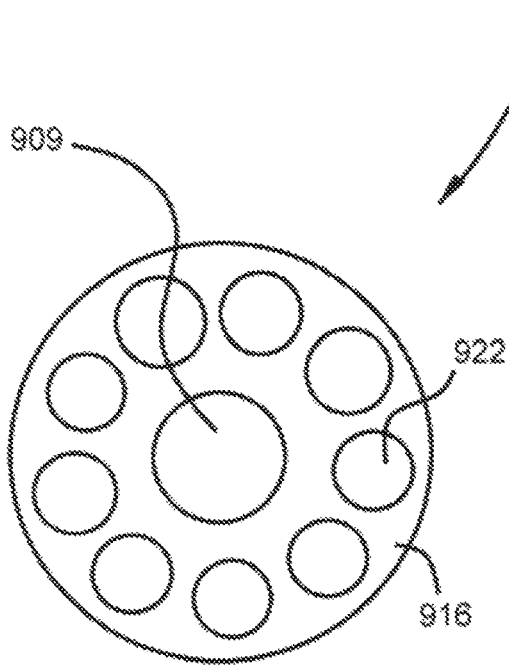
FIG. 23 is a cross-sectional view, along lines 23-23 of FIG. 27, of the plurality of passages with ablation elemental wires.

This may be most easily understood with reference to FIGS. 23-30. In this embodiment of the invention, trocar 910, like the trocars illustrated in FIGS. 20-21, include an insulative plastic cannula 916 which defines a plurality of passages for the wires which form stylets 922. As shown in FIG. 23, at the proximal end of the trocar, the wires corresponding to nine stylets 922 are arrayed in circumferential form, surrounding central axial member 909, and within passages defined by cannula 916.

Proceeding further downstream from the proximal end of trocar 910 toward the distal end of trocar 910, deflection surfaces 912 appear. As stylets 922 are advanced, their pointed ends 924 advance against surfaces 912 and stylets 922 are deflected by surfaces 912, as illustrated by stylet 922' in FIG. 24.

Figure 24:
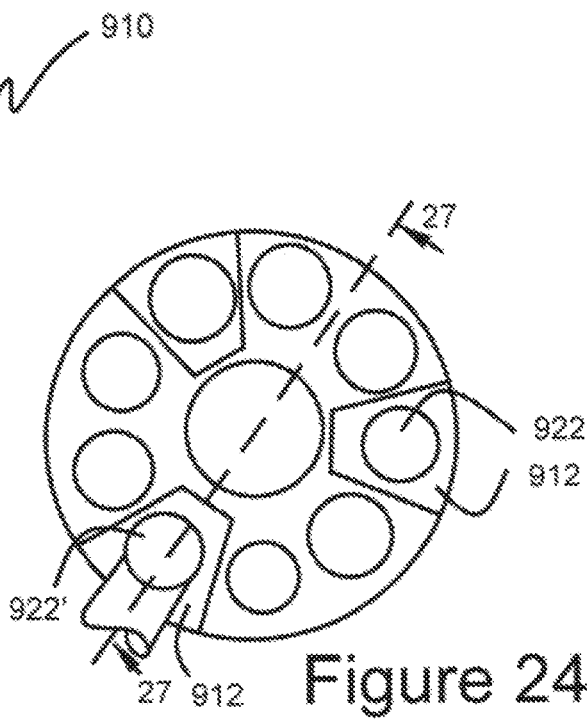
FIG. 24 is a cross-sectional view illustrating the positions of deployment for a first group of stylets.
Figure 25:
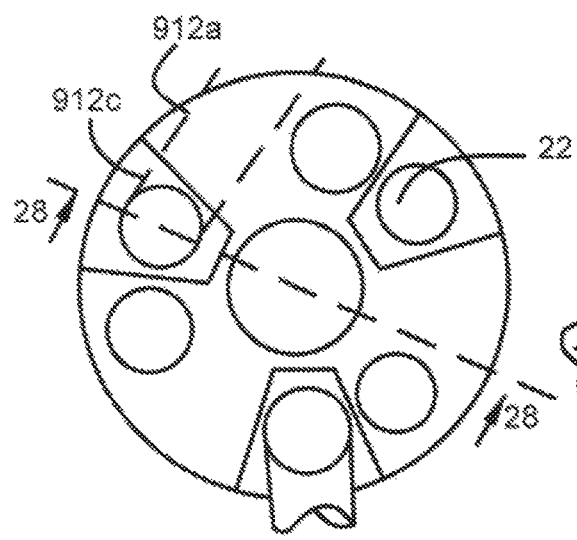
FIG. 25 is a cross-sectional view illustrating the positions of deployment for a second group of stylets.

Proceeding further downstream, only six ablation electrodes 922 remain, as illustrated in FIG. 25, on account of the exit of three electrodes at the position illustrated by the cross-section of FIG. 24. Finally, proceeding further downstream, only three ablation electrodes are positioned in cannula 916, as illustrated in FIG. 26.

Figure 26:
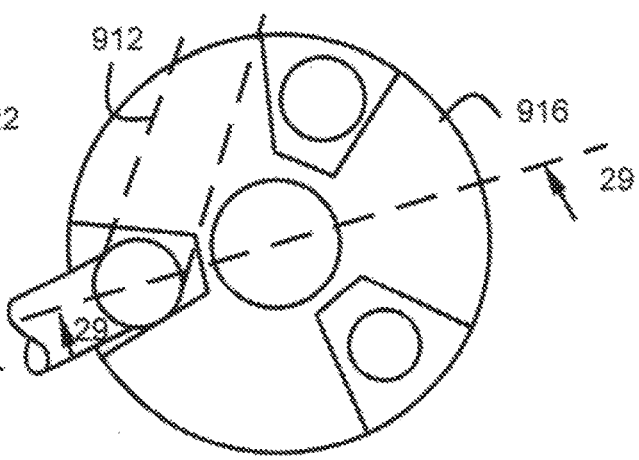
FIG. 26 is a cross-sectional view illustrating the positions of deployment for a third group of stylets.
Figure 29:
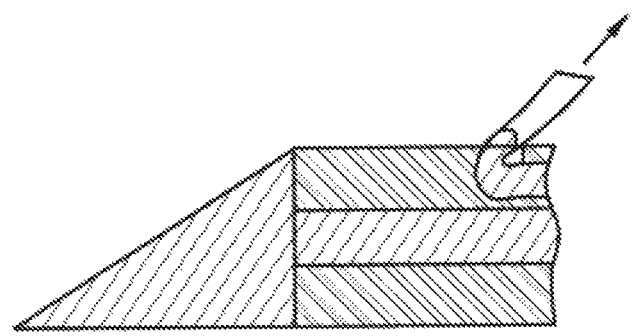
FIG. 29 is a cross-sectional view along lines 29-29 of FIG. 26.
Figure 28:
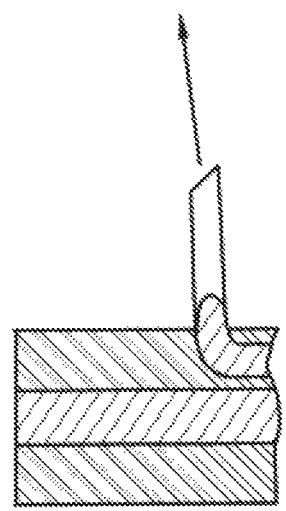
FIG. 28 is a cross-sectional view along lines 28-28 of FIG. 25.
Figure 27:
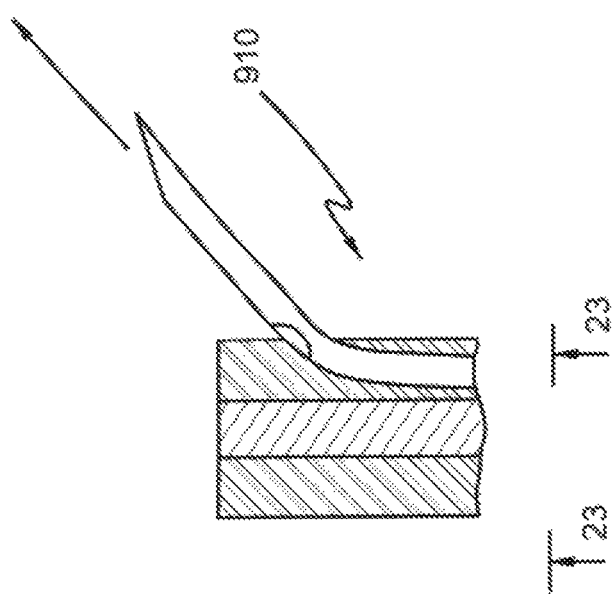
FIG. 27 is a cross-sectional view along lines 27-27 of FIG. 24.

In accordance with the present invention greater degrees of bending may be achieved by variation of the path of the trocar ablation electrodes from the simple paths illustrated in solid lines in FIGS. 24-26. More particularly, at the position illustrated in FIG. 25, the ramp 912*a* may be configured to deflect ablation electrode 922 along a longer path within the deflection member which defines the deflection surfaces. The result is a deflected shape for electrode 922*a* illustrated in phantom lines in FIG. 25. The same may be more easily understood with reference to FIG. 28. Likewise, with reference to FIG. 26, an even greater degree of the rearward bend can be achieved, as illustrated in phantom lines in FIG. 26, and in FIG. 29 by deflection by ramp surface 912*b*.

As noted above, variations in ablation volume may be achieved by varying the extent to which stylets are extended from the distal end of the trocar and the direction in which stylets extend. Still yet additional variation may be obtained by control the extension of stylets as a function of time to achieve the desired amount of tissue ablation. Such control may be achieved using electromechanical systems under the control of a microprocessor or other computing device, such as a personal computer.

Still yet another method of controlling the ablation volume after the introduction of the distal end of the trocar into the proximity of the tissue to be ablated is the extension of stylets as described above, followed by the retraction of the stylets, followed by rotation of the trocar about its axis, followed by again extending stylets as described above, followed by again retracting the stylets, and so forth until the desired ablation volume has been ablated. It is noted that in accordance with the invention, this may be done in conjunction with power control, time control, extension control and the other techniques described herein. Such rotation may be done manually by the physician, or may be automatically done by the device. Such automatic rotation and other control of stylet deployment may be done in accordance with a predetermined sequence, and/or in response to measured conditions in the tissue to be ablated, such as the measurement of temperature, resistance and so forth, and/or artificial intelligence analysis of image information. Moreover, such control may be done by direct mechanical controls, for example using position transducers to determine the a movement of stylets and angular inertial detectors to determine trocar rotation. Alternatively, imaging and feedback control may be employed.

Figure 30:
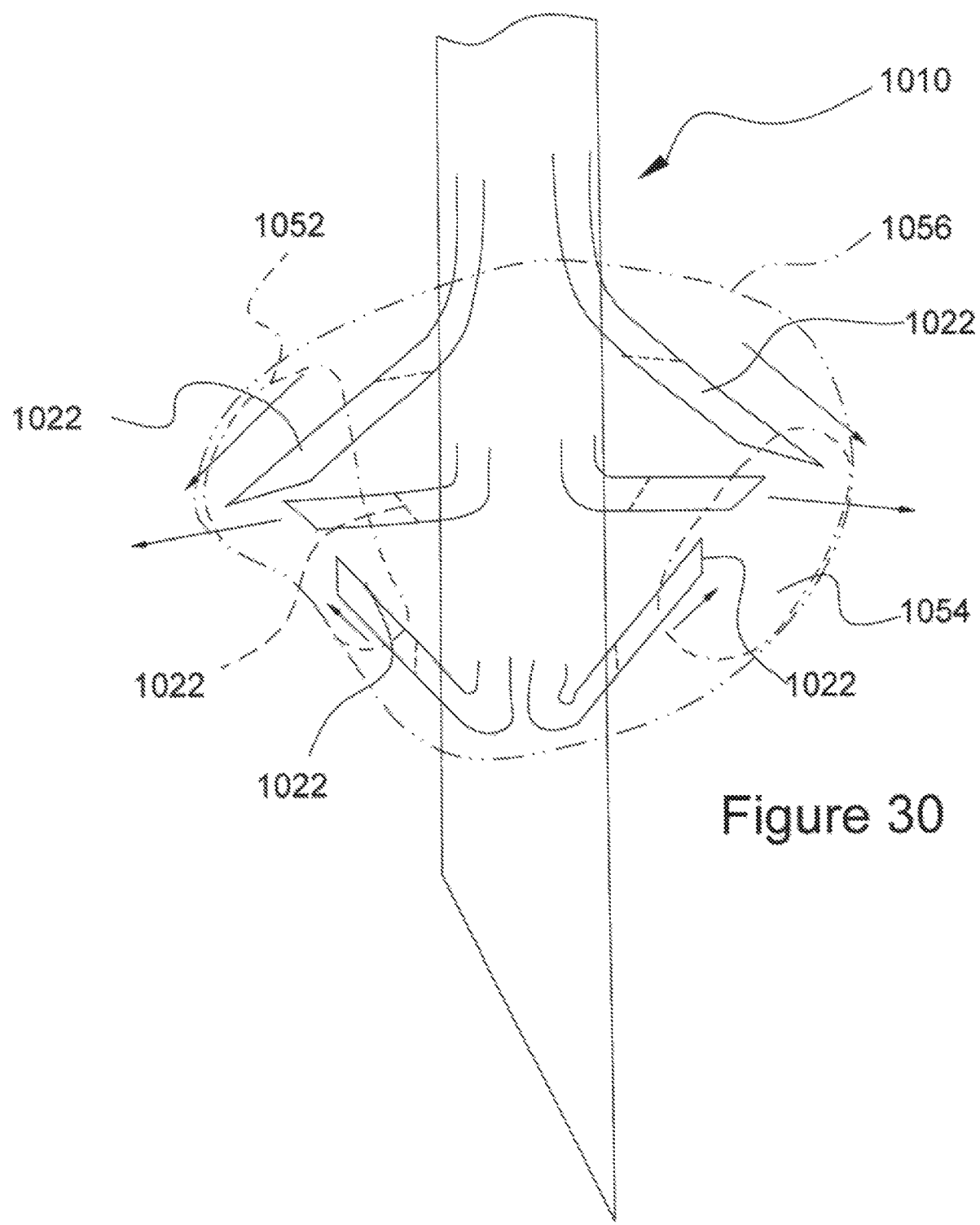
FIG. 30 is a schematic view illustrating selective ablation with multiple ablation electrode lengths and variable time exposures.

The wide range of flexibility of the inventive system may be understood with reference to FIG. 30. By way of example, trocar 1010 may initially be used to perform ablation with stylets 1022 deployed in the position as illustrated in solid lines. Electrodes 1022 would then be activated, resulting in ablation of volumes 1052 and 1054. After a period of time stylets 1022 may be withdrawn to the positions illustrated in dashed lines. Continued application of RF energy by the stylets will then ablate the remaining portion of volume 1056. Following this procedure, a relatively uniform heating of the tissue to be ablated can be achieved.

In accordance with the present invention it is recognized that the tissue of the uterus is relatively fragile and that its walls are relatively thin. Accordingly, tissue damage may impair uterus functionality during pregnancy and increase the likelihood of a loss of a pregnancy. Accordingly, a trocar structure which minimizes the size of the hole made by the trocar when it is being deployed into the body would result in significant advantages. Such an embodiment is illustrated in FIGS. 31-40.

Generally, trocar 1110 comprises a delivery surface 1112 (FIG. 40) built integrally with a trocar point 1114. Trocar 1110 comprises a plastic insulative sleeve forming a cannula 1116. Pins 1158 secure cannula 1116 to point 1114. Point 1114 include surfaces 1112 for guiding stylets 1122 into the tissue surrounding deployed ablation trocar 1110. As shown in FIG. 33, the wires which form stylets 1122 extend substantially the length of the trocar and is of minimal size for the number of stylets/anchors to be deployed. It is also noted that the wires which form stylets 1122 may be viewed as anchors, depending upon the angle at which they exit the delivery surface 1112 of point 1114.

Proceeding further downstream from the proximal to the distal end, the wires which form stylets 1122 fit into a metal or plastic superstructure associated with point 1114. Proceeding further downstream the outer surface of the catheter, previously formed by cannula 1116, is instead formatted by point 1114. In the view illustrated in FIG. 36, several of the stylets 1122 are illustrated in a deployed position. In connection with this, it is noted that, by way of example, only three of the stylets need be deployed at this point in the trocar.

Figure 38:
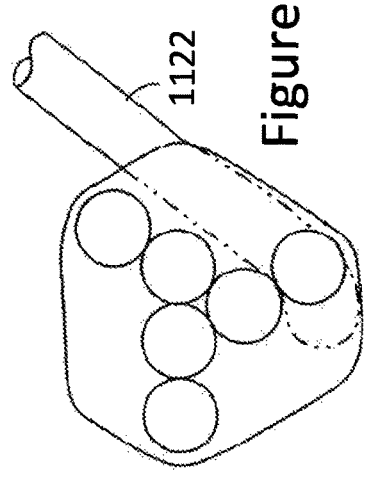
FIG. 38 is a cross section view illustrating the deployed configurations of deflection of three stylets further downstream from the position illustrated in FIG. 37.
Figure 37:
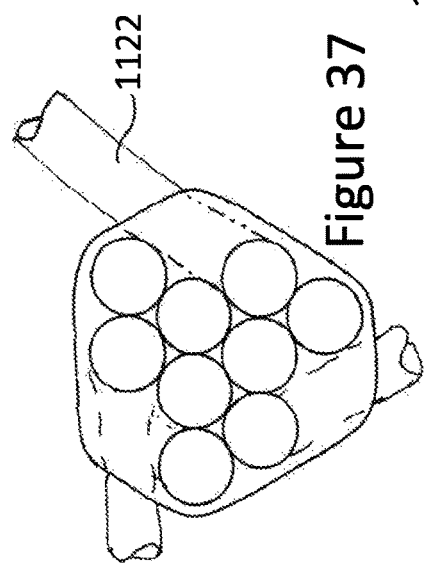
FIG. 37 is a cross-sectional view illustrating the deployed positions of three stylets further downstream from the position illustrated in FIG. 36.

However, proceeding further downstream toward the distal end of the trocar 1110, as illustrated in FIG. 37, another three stylets may be deployed. Next, as illustrated in FIG. 38, proceeding further downstream another three stylets 1122 may be deployed, leaving behind three remaining stylets/anchors. In connection with this, it is noted that the only difference in this embodiment between a stylet and an anchor is the fact that radiofrequency energy is applied to a stylet, whereas an anchor may be left in place without the application of energy. In connection with this, it is noted that an anchor to which radiofrequency energy is applied will, in addition to performing its anchoring function act as a tissue ablation electrode.

Figure 40:
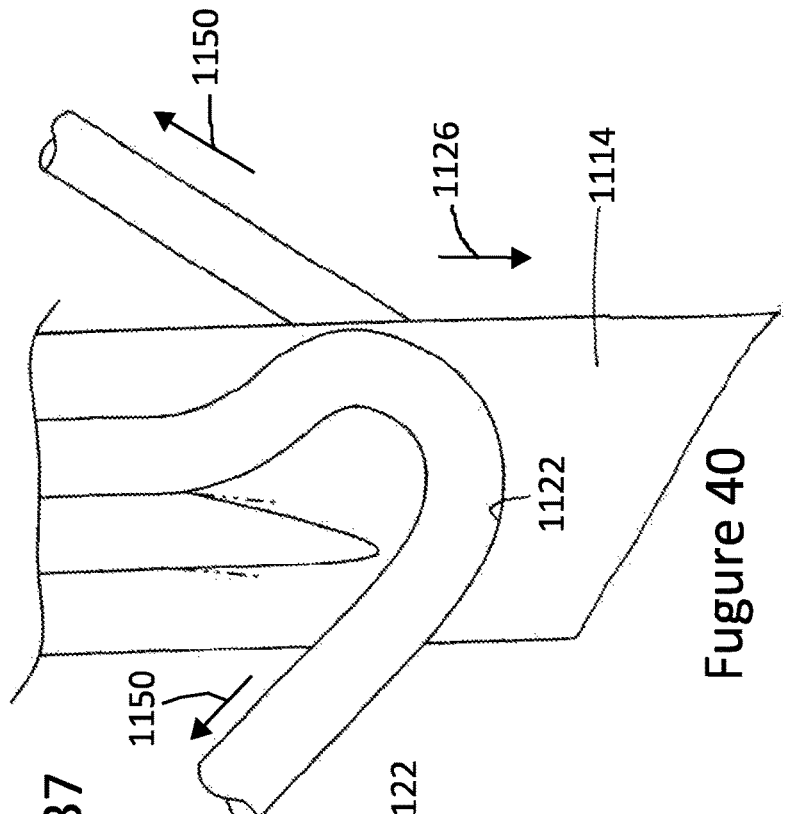
FIG. 40 is a cross-sectional view illustrating the direction of the deployed stylets.
Figure 39:
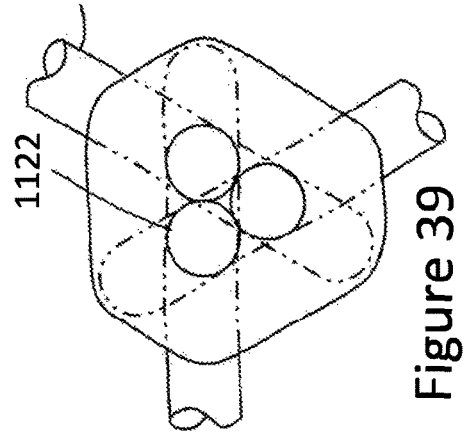
FIG. 39 is a cross-sectional view illustrating the configurations of deflection of three stylets further downstream from the position illustrated in FIG. 38.

Finally, as illustrated in FIG. 39, three stylets 1122 may be deployed as illustrated in FIG. 39 and FIG. 40. In connection with this embodiment, it is noted that these last three stylets may serve the function of also being anchors because they are advanced in the direction of arrow 1150 and thus will tend to drive trocar point 1114 forward in the direction of arrow 1126.

An even more efficient use of the width of the trocar is illustrated in FIGS. 41-44. In this embodiment trocar 1210 utilizes a cannula 1216 which is completely filled with stylets 1222. FIG. 41 illustrates the trocar 1210 at a point relatively close to the proximal end of the trocar. Two of the stylets, namely stylets 1223, act as anchors. The remaining stylets may be deployed as illustrated in FIG. 42. Thereafter proceeding further downstream, toward the distal end of the trocar, the two anchors 1223 may be deployed as illustrated in FIGS. 43 and 44.

Moreover, in accordance to present invention, other sizes and shapes of stylets may be used. For example, as illustrated in FIG. 45, a trocar 1310 may include square cross-section stylets 1322 and flat stylets 1323. Similarly, irregular shapes may be employed as illustrated in FIG. 46. Moreover, stylets may include stylets made of different materials such as materials of different conductivity. For example, anchors 1423 and stylets 1422 may be made of one material while stylets 1421 may be made of another material, perhaps having a different conductivity, flexibility, and so forth.

Figure 47:
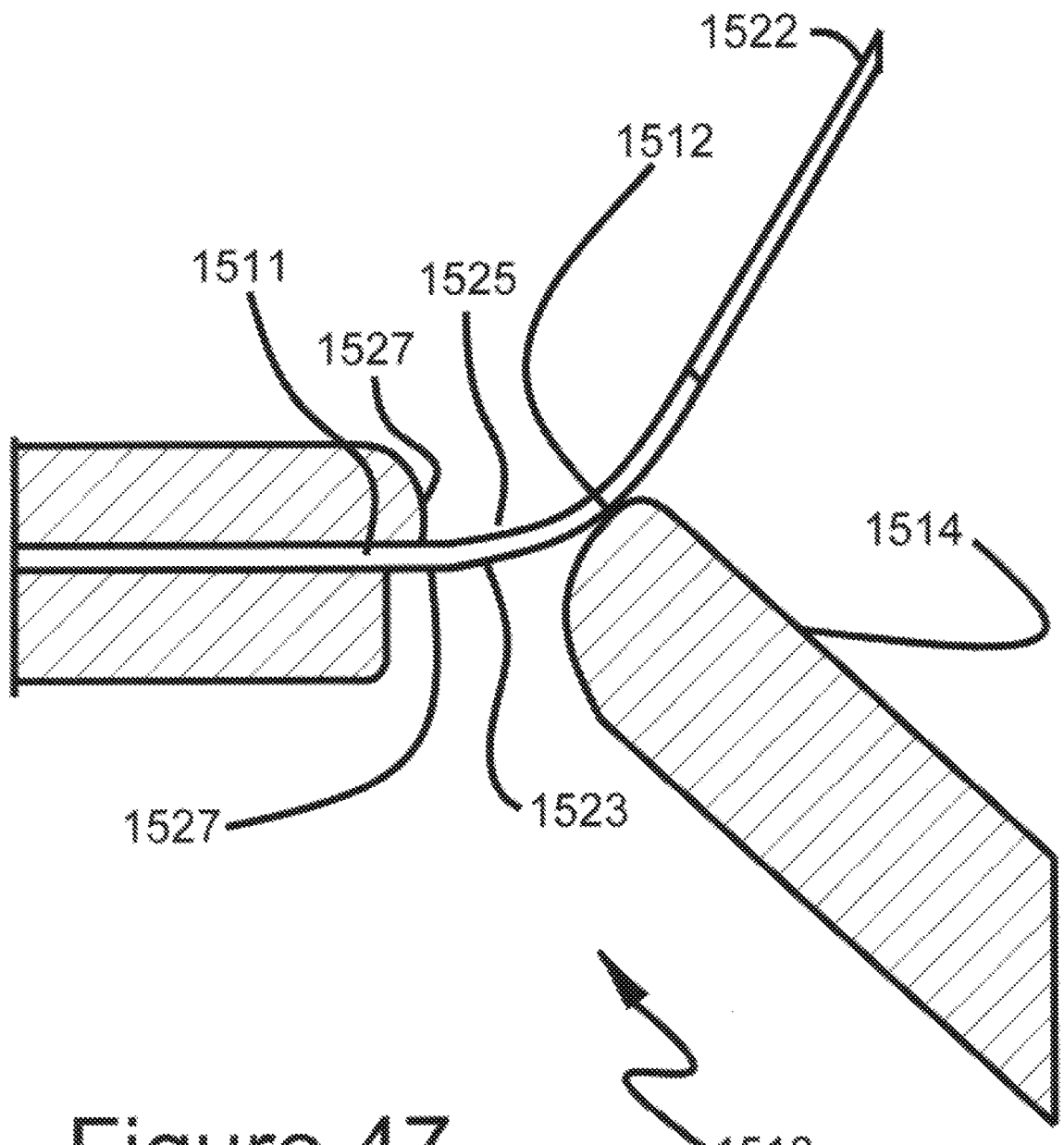
FIG. 47 is a schematic cross-sectional representation of low friction structure for advancing a stylet from the inventive trocar.

Turning to FIG. 47, a trocar 1510 includes a point 1514 which defines a first bending surface 1511 and a second bending surface 1512 which deflect stylets 1522, but which define voids 1523 and 1525, adjacent surfaces 1527 of the stylets 1522 which have no mechanical members bearing against them. This has the result of achieving low friction deflection. Generally, it is contemplated, in accordance with one possible way of implementing the invention, that friction is to be minimized by making the stylet only as thick as is necessary, for a material of the particular resiliency of the material used, to allow the stylet to be advanced through the target tissue. This results in the application of minimal force to the stylet by the deflecting members, thus reducing friction.

At the same time, the surfaces doing the deflecting are not a single continuous surface. Rather, two (and optionally more) deflection surfaces are positioned to deflect the stylet while at the same time relying on the natural tendency of the springy metal of which the stylet is made, to assume a particular radius. This takes advantage of in the inventive concept of deflecting the stylet without the need for having a substantially continuous surface in contact with the stylet.

Point 1614 may be driven during trocar withdrawal by a relatively high RF signal to cauterize the entry wound.

Figure 48:
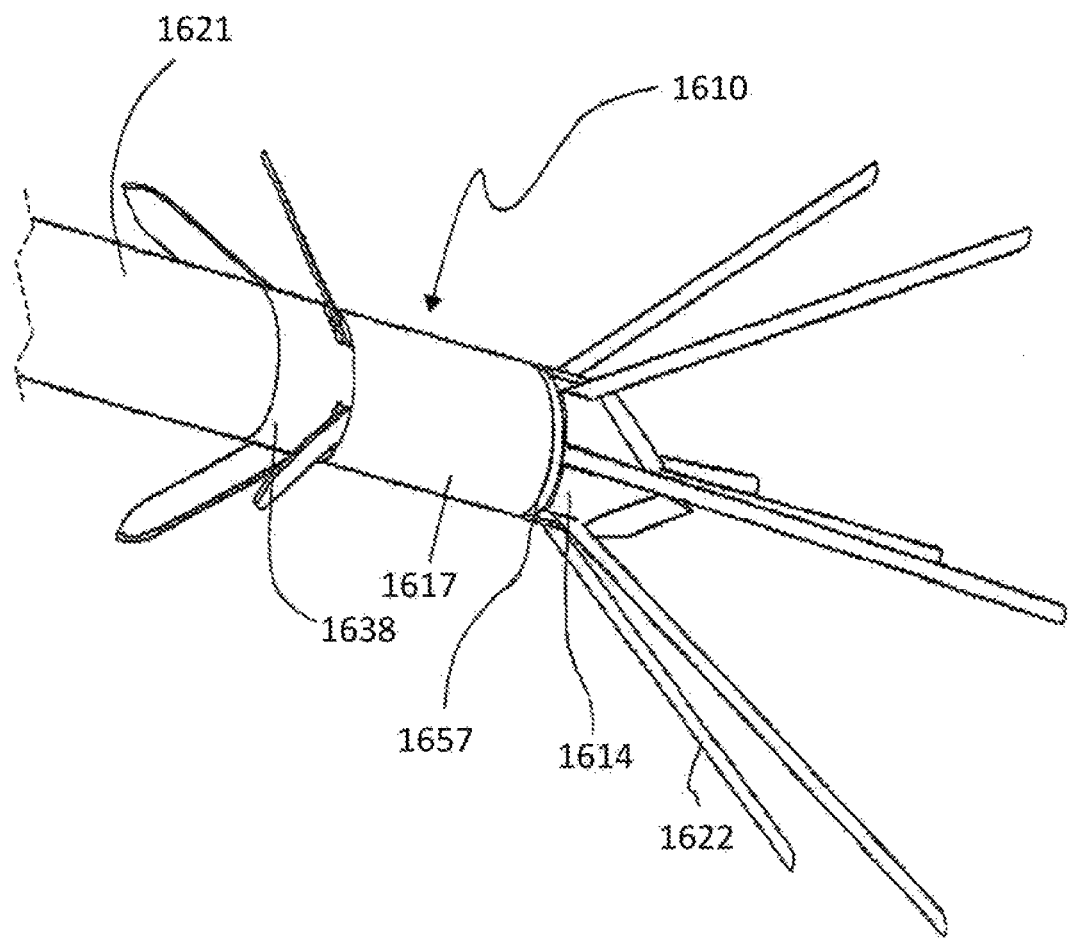
FIG. 48 is a perspective view of an alternative embodiment of the invention.
Figure 49:
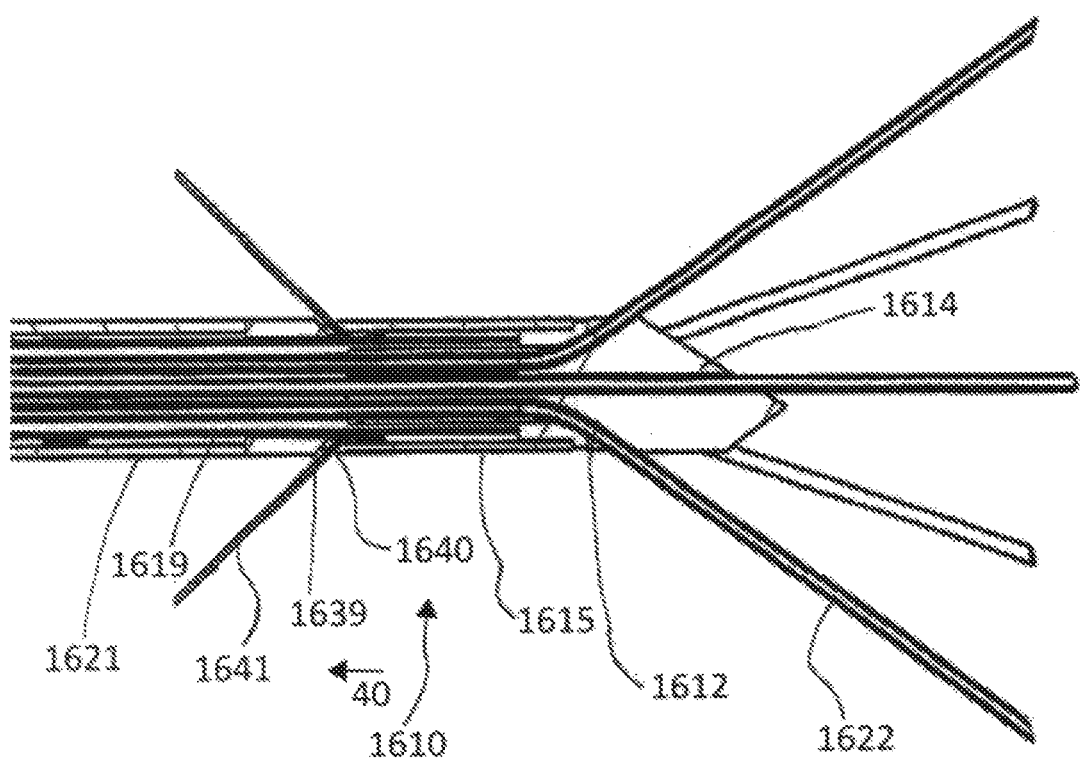
FIG. 49 is a cross-sectional view of the embodiment of FIG. 48.
Figure 50:
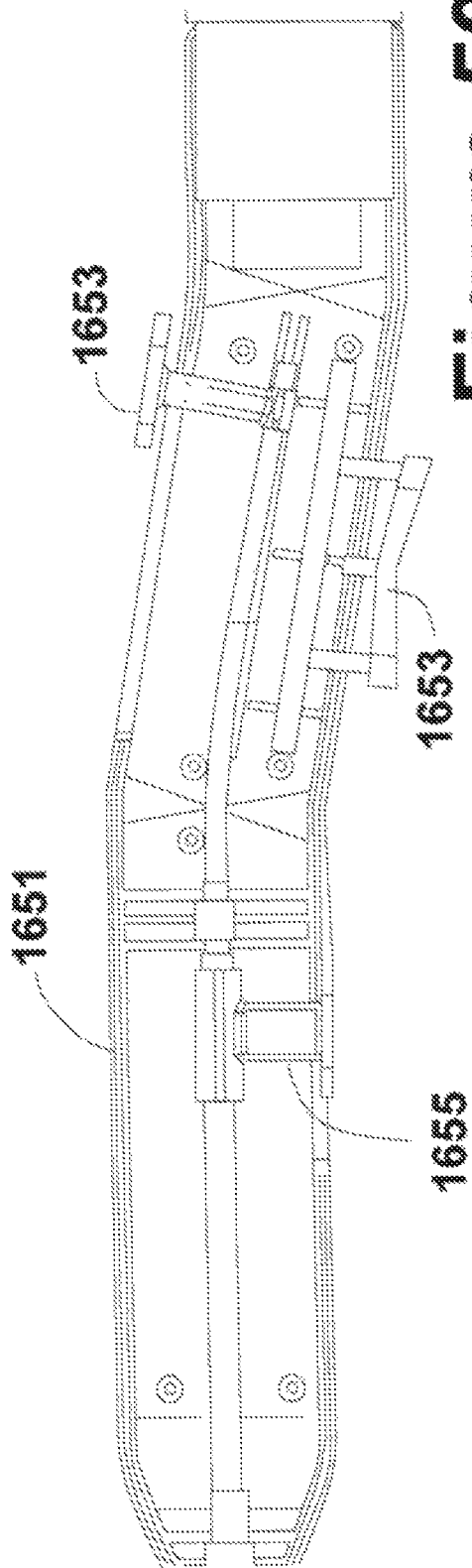
FIG. 50 is a cross sectional view of an operator handle useful with the embodiment of FIG. 48 and of 49.

Referring to FIG. 48-50, an alternative design for a trocar 1610 in accordance with the invention is illustrated. Deflection surfaces 1612 are defined in a trocar point 1614 and provide for the deflection of stylets 1622. Trocar point 1614 is secured to a hypotube 1615. The outside surface 1617 of hypotube 1615 is coated with an insulative material. Hypotube 1615 is made of metal in accordance with the preferred embodiment on account of the strength of metal having the relatively small dimensions required by the inventive trocar. While other materials may be used, presently it is preferred, in the subject embodiment and the other embodiments illustrated in the application, that the inventive trocar incorporate cannulas made of metal.

Hypotube 1615 houses a plurality of metal members whose ends form stylets 1622.

Hypotube 1615 is slidably mounted within a second cannula or hypotube 1619 whose outside surface 1621 is also coated with an insulative material. Hypotube 1619 is also preferably made of metal on account of the stiffness and strength of the metal.

Hypotube 1619 is rigidly secured to deflection member 1638. Deflection member 1638 includes a deflection surface 1639 and a counter surface 1640 between which anchor members 1641 are deflected. More particularly, when deflection member 1638 moves in the direction of arrow 40 with respect to hypotube 1615, it causes anchors 1641 to be deflected from a straight orientation parallel to the axis of trocar 1610 (similar to the position of anchors 34 in FIG. 3) to the position illustrated in FIGS. 48 and 49.

Relative motion of the two hypotubes is achieved by use of a handle 1651 incorporating a first slider member 1653 coupled to hypotube 1615, and a second slidably mounted member 1655 coupled to hypotube 1619. Hypotubes 1615 and 1619 are slidably mounted within handle 1651 and are rigidly coupled to slider members 1653 and 1655, respectively, thus providing for movement of these members at the ablation end of trocar 1610 illustrated in FIGS. 48 and 49. Power to the stylets 1622 is provided by any suitable source coupled to connector 1655.

If desired, an insulative member in 1657 may be provided to ensure electrical isolation between trocar point 1614 and deflection member 1638.

Figure 51:
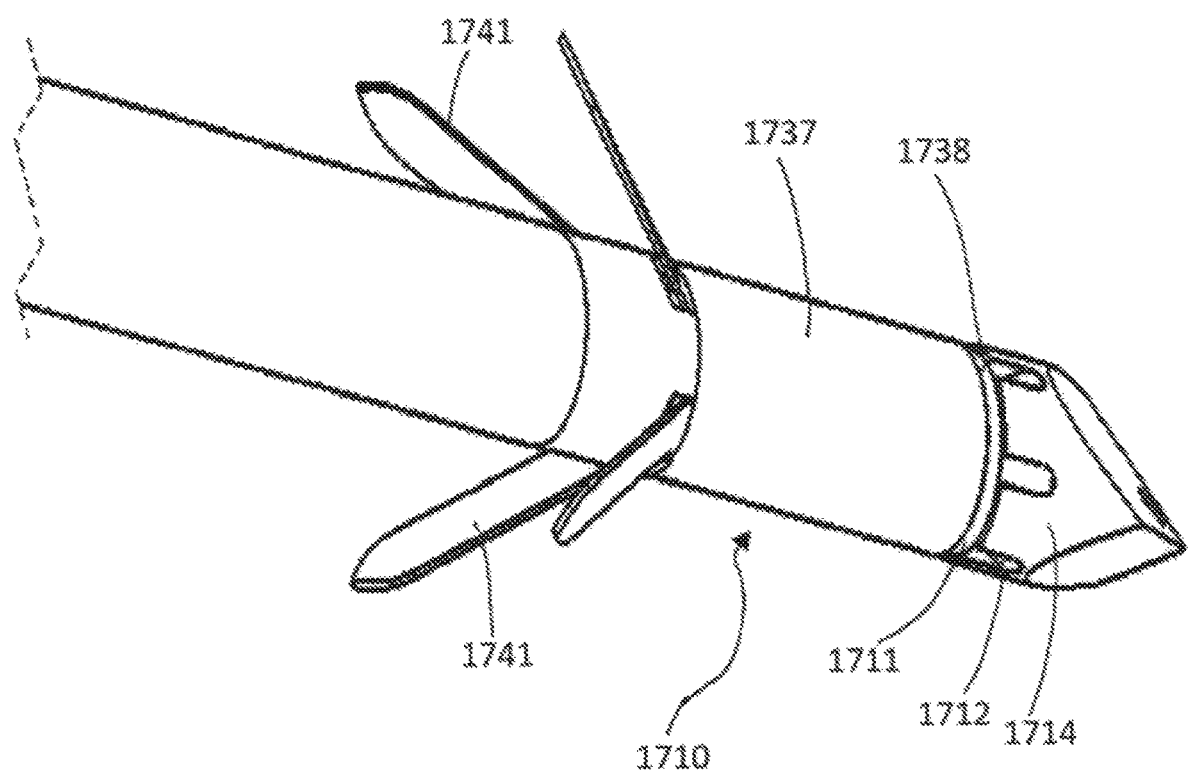
FIG. 51 is a perspective view of still another alternative embodiment of the invention.

Yet another alternative embodiment of the invention is illustrated and FIG. 51. In this embodiment, a trocar 1710 including a plurality of deflection surfaces 1712 defined in a trocar point 1714 and countersurfaces 1711 on member 1738. Deflection of anchors in 1741 is performed by a slidably mounted Teflon member 1737, mounted on a hypotube which may be drawn away from the handle at the distal end of trocar 1710 to deploy anchors 1741 as illustrated in FIG. 51.

While illustrative embodiments of the invention have been described, it is, of course, understood that various modifications will be obvious to those of ordinary skill in the art in view of the teachings of this specification. Such modifications are within the spirit and scope of the invention as limited and defined only by the appended claims.

While the inventive device has been illustrated for use in the ablation of uterine fibroids, it is understood that this particular implementation is exemplary and that the inventive device may be employed in a wide variety of circumstances.

The invention claimed is:

1. An ablation instrument, comprising:
 (a) an elongated cannula having a proximal portion and a distal portion, said cannula defining an internal lumen within said cannula and said cannula defining a cannula axis;
 (b) at least one conductor extending along at least a portion of the length of said lumen, said conductor having a proximal portion proximate the proximal portion of said cannula, and a distal portion proximate the distal portion of said cannula;
 (c) a plurality of ablation stylets each having a proximal portion, a distal portion, and a curved surface, each of said stylets coupled at the respective proximal portion of each of said stylets to the distal portion of said conductor, said stylets comprising a resiliently deflectable material said conductor together with said stylets being mounted for axial movement along at least a portion of said conductor and stylets, said ablation stylets having a substantially straight configuration in the absence of the application of external forces;

(d) a head positioned proximate to the distal portion of said cannula, said head being secured proximate the distal portion of said cannula, said head having a proximal portion and a distal portion, and said distal portion of said head comprising a head end;

(e) deflection surfaces positioned between said head end and said proximal portion of said cannula, said deflection surface being positioned closer to said head end, the deflection surfaces each being configured and positioned, in response to axial movement of said stylets, to deflect via a plurality of ramps guiding at least some of said stylets laterally and only outwardly along paths which extend away from said cannula axis causing said stylets to exit said deflection surfaces and move along substantially straight external paths external to said cannula and head, deflection by said deflection surfaces achieving most of the deflection in the path of the stylets and each of said stylets are configured to assume a substantially straight configuration in the absence of external forces; and (f) an anchor mounted in said instrument, said anchor extending rearwardly when within said instrument for movement between an internal position disposed within said instrument and an anchoring position wherein said anchor extends radially outwardly from said instrument and external of said lumen.

2. An ablation instrument as in claim 1, wherein said conductor is selected from the group consisting of electrical conductors, radio frequency conductors, microwave conductors and optical conductors.

3. An ablation instrument as in claim 1, wherein each of said conductors is integral with its respective ablation stylet.

4. An ablation instrument as in claim 1, further comprising:

(f) a motor member or members coupled to said conductors to drive axial movement of said stylets in directions from said proximal end of said cannula to said distal end of said cannula, and from said distal end of said cannula to said proximal end of said cannula through a plurality of positions.

5. An ablation instrument as in claim 1, wherein said head end is defined at the distal end of a trocar member, said trocar member having an outside surface, and said cannula having an outside surface, said trocar member having a proximal end secured proximate to the distal end of said elongated cannula and a distal end which a defines a trocar point.

6. An ablation instrument as in claim 5, wherein said deflection surface comprises a number of ramps defined proximate the proximal end of said trocar point, the distal ends of said stylets being positionable proximate to said ramps and at least partially within said trocar.

7. An ablation instrument as in claim 6, wherein said conductor is an electrical conductor, and said stylets are electrical conductors.

8. An ablation instrument as in claim 7, wherein said cannula is secured to said trocar member with the outside surface of said cannula proximate to the outside surface of said trocar member.

9. An ablation instrument as in claim 1, further comprising:

(g) a drive member disposed within said lumen and coupled to said anchor to drive said anchor between said internal position and said anchoring position.

10. An ablation instrument as in claim 9, wherein said anchor comprises at least two pointed members mounted for movement in directions which have vector components which extend away from the axis of said cannula and away from each other and rearwardly and away from head.

11. An ablation element, comprising:

(a) an elongated cannula having a proximal end and a distal end, said cannula defining an internal lumen within said cannula and a cannula axis;

(b) a conductor contained within said lumen, said conductor having a proximal end proximate the proximal end of said cannula, and a distal end proximate the distal end of said cannula;

(c) a plurality of ablation stylets each having a proximal end, a distal end, and a curved surface, and each coupled to the conductor, said stylets comprising a deflectable material said conductor together with said stylets being mounted for axial movement and lateral deflection via a plurality of ramps guiding at least some of the stylets laterally and outwardly away from the cannula;

(d) a stylet mechanical drive member coupled to said ablation stylets;

(e) a front end proximate the distal end of said cannula;

(f) one or more anchors mounted for movement between an internal position disposed substantially within a trocar surface and an anchoring position extending laterally and/or rearwardly away from said front end and from said trocar surface through points external of said lumen; and (g) an anchor drive member separate from said stylet mechanical drive member, said anchor drive member disposed within said lumen and coupled to said anchor to drive said anchor between said internal position and said anchoring position, wherein said anchor comprises at least two pointed members mounted for movement in directions which have vector components which extend away from the axis of said cannula and away from each other.

12. An ablation element as in claim 11, wherein said front end comprises a trocar point defined at the distal end of a trocar member, said trocar member having an outside surface, said elongated cannula having an outside surface, said trocar member having a proximal end secured proximate to the distal end of said elongated cannula, and the outside surface of said elongated cannula and the outside surface of said trocar member define a trocar surface.

13. An ablation element as in claim 12, wherein said trocar member bears a deflection surface, said deflection surface comprising a number of ramps defined proximate the proximal end of said trocar point, the distal ends of said stylets being positionable proximate to said ramps and within said trocar surface.

14. An ablation element as in claim 11, wherein said anchors when positioned in said cannula extend in directions which have vector components which extend away from the distal end of said of ablation element.

15. An ablation element as in claim 11, wherein said anchors are deployed in response to rotary motion.

16. An ablation element as in claim 11, wherein said anchors are deployed by bearing against a deflection surface.

17. An ablation element as in claim 11, wherein said anchors are made of a springy material which assumes a curved configuration when not subjected to external forces.

* * * * *